(12) United States Patent
Ozdemir et al.

(10) Patent No.: US 10,782,289 B2
(45) Date of Patent: Sep. 22, 2020

(54) MICRO-RESONATOR AND FIBER TAPER SENSOR SYSTEM

(71) Applicant: Washington University, St. Louis, MO (US)

(72) Inventors: Sahin Kaya Ozdemir, St. Louis, MO (US); Lan Yang, St. Louis, MO (US)

(73) Assignee: Washington University, St. Louis, MO (US)

( * ) Notice: Subject to any disclaimer, the term of this patent is extended or adjusted under 35 U.S.C. 154(b) by 298 days.

(21) Appl. No.: 15/801,823

(22) Filed: Nov. 2, 2017

(65) Prior Publication Data

US 2018/0164307 A1 Jun. 14, 2018

Related U.S. Application Data

(63) Continuation of application No. 15/019,942, filed on Feb. 9, 2016, now abandoned.

(60) Provisional application No. 62/113,610, filed on Feb. 9, 2015.

(51) Int. Cl.

| | | |
|---|---|---|
| *G01N 21/41* | (2006.01) | |
| *G01N 33/543* | (2006.01) | |
| *G01N 15/14* | (2006.01) | |
| *G01N 21/77* | (2006.01) | |
| *G01N 21/45* | (2006.01) | |
| *G01N 15/00* | (2006.01) | |
| *G01N 21/21* | (2006.01) | |

(52) U.S. Cl.
CPC ... *G01N 33/54373* (2013.01); *G01N 15/1429* (2013.01); *G01N 15/1434* (2013.01); *G01N 15/1463* (2013.01); *G01N 21/45* (2013.01); *G01N 21/7746* (2013.01); *G01N 21/21* (2013.01); *G01N 2015/0038* (2013.01); *G01N 2015/1454* (2013.01); *G01N 2021/458* (2013.01); *G01N 2201/0683* (2013.01); *G01N 2201/06113* (2013.01); *G01N 2201/08* (2013.01)

(58) Field of Classification Search
CPC .. G01N 21/41; G01N 21/4133; G01N 21/431; G01N 21/43; G01N 21/552
USPC ........................................................ 356/128
See application file for complete search history.

(56) References Cited

U.S. PATENT DOCUMENTS

| | | | |
|---|---|---|---|
| 6,018,386 | A | 1/2000 | Radun |
| 7,085,452 | B1 | 8/2006 | Lin et al. |
| 2003/0181307 | A1* | 9/2003 | Myers ..................... C03C 3/16 501/45 |
| 2011/0139970 | A1 | 6/2011 | He et al. |
| 2011/0306854 | A1 | 12/2011 | Arnold et al. |
| 2012/0268731 | A1 | 10/2012 | Zhu et al. |
| 2015/0285728 | A1 | 10/2015 | Ozdemir et al. |

OTHER PUBLICATIONS

Forstner, S. et al., "Cavity Optomechanical Magnetometer," Physical Review Letters, 108(12): 4 pages (2012).

(Continued)

*Primary Examiner* — Md M Rahman
(74) *Attorney, Agent, or Firm* — Armstrong Teasdale LLP

(57) ABSTRACT

A micro-resonator and fiber taper based sensing system, which uses mode splitting or frequency shift methods and polarization measurements for particle sensing.

2 Claims, 12 Drawing Sheets

(56) References Cited

OTHER PUBLICATIONS

Hossein-Zadeh, M. et al., "Characterization of a Radiation-Pressure-Driven Micromechanical Oscillator," Physical Review A, 74(2):023813-1 to 023813-15 (2006).
Monifi, F. et al., "Ultrasound Sensing Using a Fiber Coupled Silica Microtoroid Resonator Encapsulated in a Polymer," 2013 IEEE Photonics Conference (IPC), held in Bellevue, WA on Sep. 8-12, 2013 (2 pages).
Watts, M.R. et al., "Microphotonic Thermal Imaging," Nature Photonics, 1(11): 632-634 (2007).
Xie, Z. et al., "Pure Optical Photoacoustic Microscopy," Optics Express, 19(10): 9027-9034 (2011).
Zhu, J. et al., "Infrared Light Detection Using a Whispering-Gallery-Mode Optical Microcavity," Applied Physics Letters, 104(17): 171114 (2014).
Zhu, J. et al., "On-Chip Single Nanoparticle Detection and Sizing by Mode Splitting in an Ultrahigh-Q Microresonator," Nature Photonics, 4(1): 46-49 (2010).

\* cited by examiner

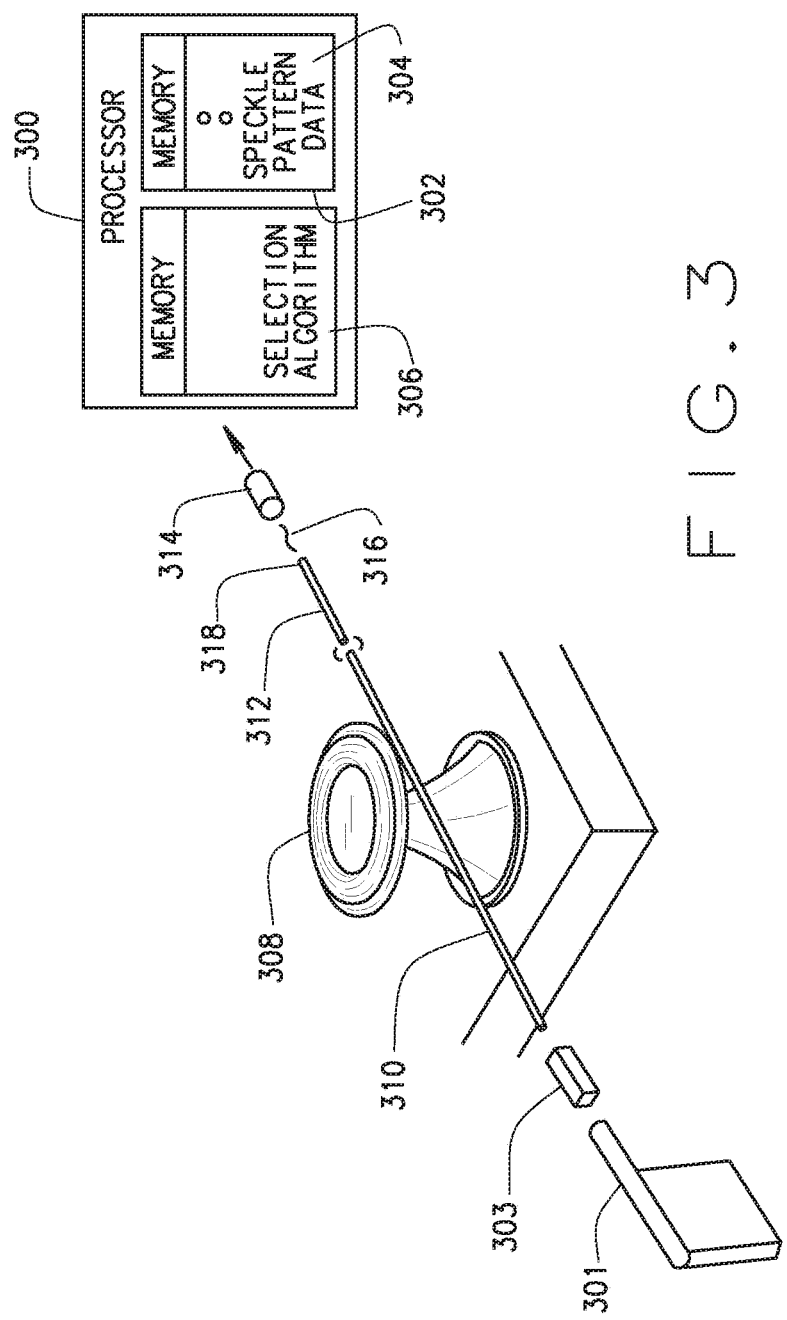

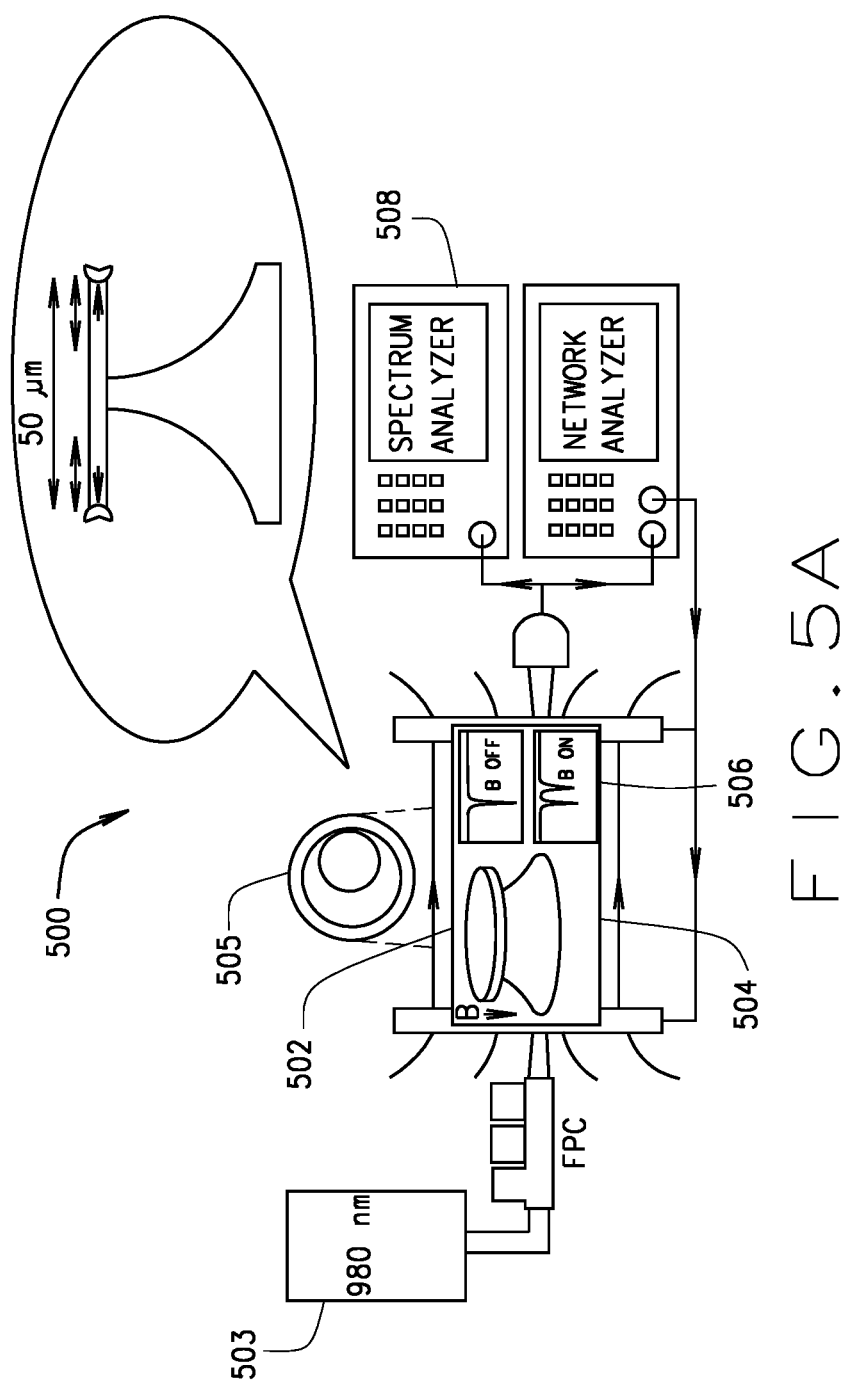

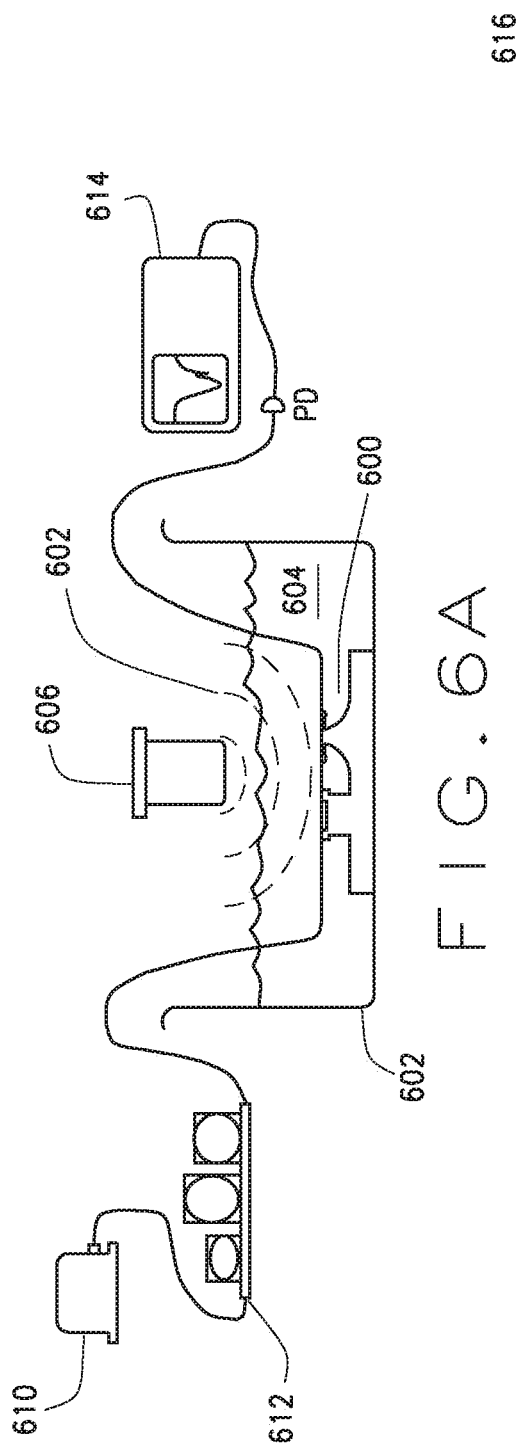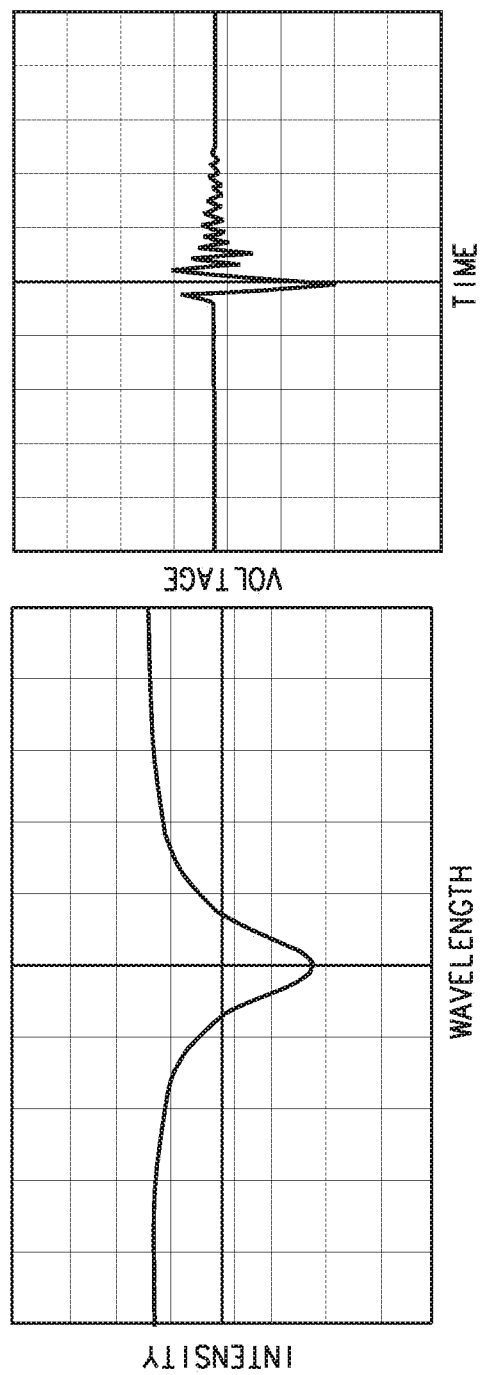
FIG. 6A
FIG. 6B
FIG. 6D

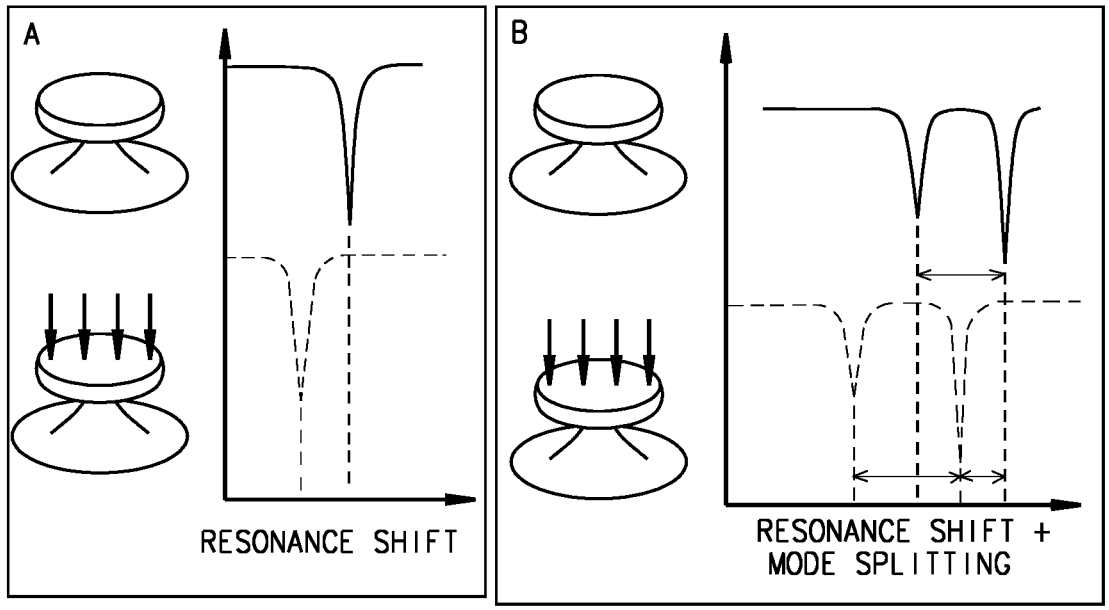
FIG. 7A
FIG. 7B
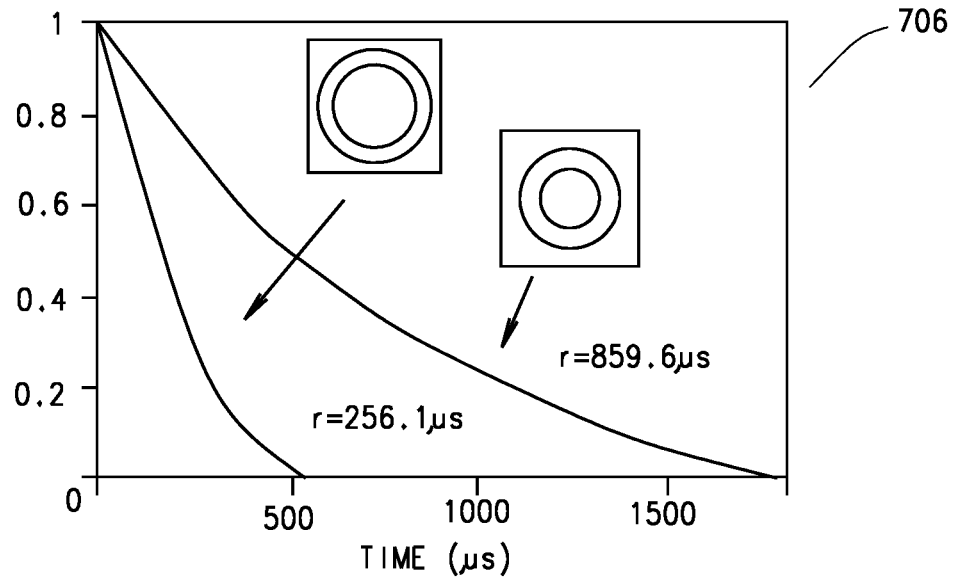
FIG. 7C

MICRO-RESONATOR AND FIBER TAPER SENSOR SYSTEM

CROSS-REFERENCE TO RELATED APPLICATIONS

This application is a continuation of U.S. application Ser. No. 15/019,942 filed on Feb. 9, 2016, entitled MICRO-RESONATOR AND FIBER TAPER SENSOR SYSTEM, the contents of which are incorporated herein in their entirety. U.S. application Ser. No. 15/019,942 claims the benefit of U.S. Provisional Application Ser. No. 62/113,610, filed Feb. 9, 2015, entitled MICRORESONATOR AND FIBER TAPER BASED SENSOR SYSTEMS, which is hereby incorporated in its entirety herein.

STATEMENT REGARDING FEDERALLY SPONSORED RESEARCH & DEVELOPMENT

This invention was made with government support under grant NSF 0954941 awarded by the National Science Foundation and grant W911NF-12-1-0026 awarded by the [U.S.] Army Research Office. The U.S. government has certain rights in the invention.

BACKGROUND

1. Field

This technology relates generally to sensing micro and nanoscale particles, and more particularly, to nanoscale sensing and wave sensing/detection using micro-resonators.

2. Background Art

Interest in nanoparticle detection and characterization techniques has increased with the increasing awareness of the potential benefits and risks of the continuously generated byproduct or massively synthesized nano-particles. Nano-particles of special interests range from biological agents and virions to specially synthesized semiconductor, metal, and polymer nanoparticles. Detection and characterization of biological agents and virions is important for biodefense applications and early detection of pandemic outbreaks, while detection and characterization of synthesized nano-particles is important for a broad range of applications in nanotechnology.

At least some known particle detection systems use conventional microscopic techniques which, despite their high sensitivity and resolution, may not be suitable for field measurements due to their expensive and bulky constructions, long processing times, and the necessity of pretreatment (labeling with fluorescent dyes, etc.) of the particles. Further, at least some known optical particle counters use light scattering measurements to allow field measurements and detect and count individual particles or groups of particles. These counters generally require off-axis detectors for the collection of the scattered light, bulky configurations, and relatively sophisticated signal processing components.

There is a growing interest for nanoparticle detection using nano and micro-scale sensors, which, with relatively high sensitivity, also have the potential for in-situ sensing. Some nano/micro-scale sensors detect particles by monitoring resonance frequency changes caused by additional effective mass of binding particles, while resonator-based micro/nano-optical resonator sensors rely on either resonance frequency shift or mode splitting due to changes in the effective polarizability of the resonator system upon particle binding. Optical devices fundamentally rely upon interactions between light and the matter being detected. The more increase in light to matter interaction new phenomena can be detected because of higher resolution and as a result new functionalities of these sensors can be developed. For micro-resonators interactions increase because light circulates in a resonator multiple times with minimal loss.

Photonic technologies on one hand have brought about new concepts in materials and devices such as photonic crystals and meta materials, and, on the other hand, brought about the realization and testing of century-old well known theories such as quantum theory, plasmonics and whispering galleries which have been enjoying many benefits of recent developments in enabling technologies and fabrication techniques. Since its first explanation in acoustic regime by Lord Rayleigh in London's St Paul's Cathedral, Whispering Gallery Mode (WGM) phenomenon has been explored in various optical structures for a variety of applications, opening unprecedented and unforeseen directions in optical sciences.

Resonator-based sensors have shown to detect and count individual nanoparticles having a radius as small as radius 30 nanometers (nm). This high sensitivity is attributed to the resonance-enhanced interaction between the particle and the evanescent tail of the light field due to tight light confinement and extended interaction time provided by the resonator. These sensors generally require a fiber taper to couple the light into and out of the resonator from a tunable laser, whose wavelength is continuously scanned to monitor the changes in the resonance modes, thus making these highly compact and sensitive sensors relatively expensive.

An optical cavity, also called an optical resonator, is an arrangement of mirrors that forms a standing wave cavity resonator for light waves. Optical cavities are a major component of lasers, surrounding the gain medium and providing feedback of the laser light. Light confined in the cavity reflects multiple times producing standing waves for certain resonant frequencies. The standing wave patterns produced are called "modes". Longitudinal modes differ only in frequency while transverse modes differ for different frequencies and have different intensity patterns across the cross-section of the beam. Constructive or destructive interference between multiple reflections between two or more reflecting surfaces can occur. Resonance Condition 2 $nL = m\lambda$.

To understand how optical ring resonators work, one must first understand the optical path length difference (OPD) of a ring resonator. This is given as follows for a single-ring ring resonator:

$$OPD = 2\pi r n_{eff}$$

where r is the radius of the ring resonator and $n_{eff}$ is the effective index of refraction of the waveguide material. Due to the total internal reflection requirement, $n_{eff}$ must be greater than the index of refraction of the surrounding fluid in which the resonator is placed (e.g. air). For resonance to take place, the following resonant condition must be satisfied:

$$OPD = m\lambda_m$$

where $\lambda_m$ is the resonant wavelength and m is the mode number of the ring resonator. This equation means that in order for light to interfere constructively inside the ring resonator, the circumference of the ring must be an integer multiple of the wavelength of the light. As such, the mode number must be a positive integer for resonance to take place. As a result, when the incident light contains multiple wavelengths (such as white light), only the resonant wavelengths will be able to pass through the ring resonator fully.

The quality factor of an optical resonator can be quantitatively described using the following formula:

Quality Factor:

$$Q = 2\pi \frac{\text{stored energy}}{\text{energy lost per cycle}}$$

The quality factor is useful in determining the spectral range of the resonance condition for any given ring resonator. The quality factor is also useful for quantifying the amount of losses in the resonator as a low Q factor is usually due to large losses.

WGMRs are a type of optical cavity resonator but they do not have mirrors (i.e., mirror-less cavities). WGMRs can support two counter-propagating modes at the same resonance frequencies. Unless these counter-propagating modes are coupled strongly to each other (for example by scattering via defect centers, scatterers or structural inhomogeneities), the wave inside a WGMR is a travelling wave. When the counter propagating modes are coupled to each other, they form a standing wave mode. Interaction strength in a micro-resonator is a function of the spectral Quality Factor (Q) and Spatial Volume (V), which will define the energy density within the cavity. It is desirable to have a high Q, while maintaining a smaller mode volume V.

Whispering-gallery waves, (i.e. whispering-gallery modes), are a type of wave that can travel around a concave surface. Whispering-gallery waves exist for light and sound waves. While they propagate light and sound waves (i.e., any type of waves), they form patterns called modes. Optical whispering-gallery-modes have been produced in microscopic glass spheres, micro-disks, micro-toroid, micro-bottle, etc. . . . structures, for example, with applications in lasing and sensing. In such structures, the light waves are almost perfectly guided by optical total internal reflection, leading to Q factors in excess of $10^{10}$ being achieved. Whispering Gallery Mode Resonators (WGMRs) resonate, i.e. have a tendency to oscillate with greater amplitude at some frequencies more so than at others, at certain frequencies. Frequencies at which the response amplitude is a relative maximum are known as the system's resonant frequencies, or resonance frequencies. At these frequencies, even small periodic driving forces can produce large amplitude oscillations, because the system stores energy.

Whispering-gallery-mode (WGM) micro-resonators with their high quality factor, Q, and small mode volume, V, are known to enhance light-matter interactions and have extraordinary sensitivities to changes and perturbations in their structure or proximity. They have been of great interest for sensing biomarkers, DNA, and medium-size proteins at low concentrations, as well as for detecting viruses and nanoparticles at single-particle resolution. A particle or molecule entering the mode volume of a resonator or binding onto its surface induces a net change in the polarizability of the resonator-surrounding system and perturbs its optical properties. This manifests itself as a shift of the resonance frequency, broadening of the resonance linewidth, or formation of a doublet via mode splitting depending on the interaction strength and the scattering and absorption properties of the binding particle or the molecule.

In WGM sensors, the fundamental limit of sensitivity is determined by Q/V, which quantifies the strength of the interaction between the particle and the cavity field. Thus, it can be improved by decreasing V or increasing Q. One can increase Q by compensating for the losses and decrease V by shrinking the size of the WGM resonator (WGMR). However, decreasing the resonator size below a critical value inevitably increases bending losses and eventually decreases Q. Instead, hybrid systems combining high-Q WGMs with highly confined (small-V) localized plasmons have been demonstrated, achieving detection of single proteins and very small viruses. Q enhancement of WGM resonances by compensating losses via optical gain has also been demonstrated in silica micro-toroids doped with rare-earth ions such as erbium (Er3+) and ytterbium (Yb3+). Resonators with optical gain are referred to as active resonators.

Optical whispering-gallery-mode resonators (WGMRs) have emerged as promising platforms for label-free detection of nano-objects. The ultimate sensitivity of WGMRs is determined by the strength of the light-matter interaction quantified by quality factor/mode volume, Q/V, and the resolution is determined by Q.

Quality Factor:

$$Q = 2\pi \frac{\text{stored energy}}{\text{energy lost per cycle}}$$

The less energy lossed during light circulation within the resonator, the higher the Quality factor. The Electric Field in the cavity can be defined by:

$$E(t) = E_0 \exp\left(i\omega t - \frac{\omega}{2Q}t\right) \Rightarrow$$

$$|E(\omega)|^2 \propto \frac{1}{(\omega - \omega 0) + (\omega 0/2Q)^2} \Rightarrow$$

Linewidth of a resonance: $\Delta\omega = \omega_o/Q$

Quality Factor $Q = \omega_o/\Delta\omega$

To improve the sensitivity and the precision of detection, WGMRs have been either doped with rare-earth ions to compensate for losses and increase Q; or plasmonic resonances have been exploited for their superior field confinement and lower V. In addition to rare-earth ions, previous whispering gallery mode (WGM) micro-laser based particle detection methods utilized quantum dot(s) or optical dye(s) as dopant(s) into the WGM resonator. Use of dopants make the fabrication process complicated (i.e., one has to find ways of doping the resonators), costly (rare-earth ions, quantum dots and dyes are expensive, and new fabrication processes add to the cost) and introduce biocompatibility issues.

For example, silica is a biocompatible material; however, rare-earth-ions are not biocompatible. Therefore, doping silica WGM resonator with a rare-earth-ion destroys biocompatibility. Moreover, each rare-earth ion, quantum dot or optical dye can be used only for a specific wavelength band (each has its own pump laser wavelength band and emission band). For each different wavelength band of operation a different rare-earth ion and a different pump laser should be used. The benefit of ultra-high Q silica micro-cavities can be seen by examining the cavity power build-up factor.

$$B = \frac{P_{cav}}{P_{in}} = \frac{\lambda Q}{2\pi^2 nD}$$

And the cavity photon lifetime:

$$\tau = \frac{Q}{\omega}$$

$Q=1\times10^8$, $D=50$ μm, $V_m=650$ μm$^3$=>$B=1.1\times10^5$
$P_{in}=1$ mW=>
$P_{cav}$~110 W, $I_{cav}$~2.5 GW/cm$^2$,
$\tau$~100 ns, # of round trip~$2\times10^5$.

Recent advances in fabrication techniques and material sciences have helped to achieve Whispering Gallery Mode Resonators (WGMRs) with ultra-high-quality (Q) factors and nano/micro-scale mode volumes (V), which in turn have enabled novel applications and devices such as ultra-low threshold on-chip micro-lasers, narrowband filters and modulators for optical communication, high performance optical sensors achieving label free detection at single-particle resolution, cavity opto-mechanics, and quantum electrodynamics. The Q factor or quality factor is a dimensionless parameter that describes how under-damped an oscillator or resonator is, or equivalently, characterizes a resonator's bandwidth relative to its center frequency. Higher Q indicates a lower rate of energy loss relative to the stored energy of the oscillator, i.e., the oscillations die out more slowly.

When such a WGMR is optically pumped above lasing threshold, the resultant laser has a narrower linewidth than the cold cavity and thereby improves the detection limit and sensitivity beyond what can be achieved by the passive (no optical gain-providing mechanism) or by the active resonator below the lasing threshold. However, fabricating WGM-plasmon hybrids and active WGMRs with dopants introduces additional processing steps and costs. For example, WGM-plasmon hybrids require preparation and adsorption of plasmonic nano-structures onto the resonator surface, and active resonators suffer from the fact that most rare-earth ions are not biocompatible and that for each different wavelength band of operation a different rare-earth ion and a different pump laser should be used. It is desirable to accomplish label free real-time detection and sensing of nano-scale particles with minimum assumptions surrounding shape, RI, viscosity, or thermal characteristics. It is desirable that the sensing system would be highly accurate and have high resolution with a single particle and with a small sample size with a large dynamic range and that is able to work in an air or aqueous environment. Various system and method for leveraging the favorable characteristics of WGMRs continue to emerge. The subject matter of this application addresses applications of these favorable characteristics.

BRIEF SUMMARY

The technology as disclosed uses mode splitting or frequency shift methods for particle sensing. Particle selectivity can be based on a polarization measurement which can be performed on each detected particle with single-shot measurement. Also, it is possible to develop portable and on chip sensors based on micro-resonator technology. Use of a polarizer to operate on a laser can provide for greater mode selection and optimize performance.

Mode splitting in high-Q WGM resonators is an alternative to resonance-frequency-shift method and has been demonstrated to yield label-free and highly sensitive detection of particles with radii as small as 30 nm with single particle resolution. Mode splitting occurs due to the coupling of counter-propagating doubly degenerate WGMs via the scattering of light from a sub-wavelength scatterer entering the resonator mode volume. This modal coupling lifts the degeneracy and creates two standing wave modes whose resonance frequencies and linewidths differ by $$2|g|=-\alpha f^2(r)\omega/V \text{ and}$$

$$2\Gamma_R=-\alpha^2 f^2(r)\omega^4/(3\pi v^3 V), \text{ respectively.}$$

Here, the polarizability α is defined as $\alpha=4\pi R^3(n^2-n_e^2)/(n^2+2n_e^2)$, for a single particle of radius R and refractive index n in the surrounding medium of refractive index ne, $f^2(r)$ is the normalized mode distribution, v is the speed of light in the medium, and $\omega=2\pi c/\lambda$, is the angular frequency of the resonant, λ and c being the wavelength of WGM before splitting and the speed of light in vacuum, respectively. Polarizability of a scatterer is calculated as $\alpha=-(\Gamma/g)(\lambda/n_e)(3/8\pi^2)$ from which one can estimate the size. Advantages of mode splitting method over the resonance-frequency-shift method are the accurate estimation of the size regardless of the location of the particle in the resonator mode volume and the robustness of the mode splitting spectra against interfering perturbations (e.g., laser and detector noises, temperature fluctuations which uniformly affect the resonator).

Mode splitting can be leveraged in air where it is easier to satisfy the mode splitting resolvability criterion $2|g|>\Gamma+(w/Q)$ as well as in aqueous environments. Mode splitting in aqueous environments allow for diverse applications, such as bio-chemical and bio-molecular sensing, detection and characterization of nanoparticles in liquid solutions.

One implementation of the technology is a particle sensing apparatus including a processor and a memory having data representative of plurality of polarizability values for a plurality of common air pollutants and the memory can have a selection algorithm. The technology can include a tunable laser, a mode-splitting based whispering gallery mode micro-resonator, and a coupled waveguide configured to transition the tunable laser in and out resonance modes. A photodetector can be configured to detect a laser signal output at an output port of the coupling waveguide and said photodetector having a detector output signal representative of the detected laser signal output. The processor can be configured to process the selection algorithm to analyze a transmission spectrum of the detector output signal, thereby deriving a detected polarizability value and selecting a matching polarizability value from the plurality of polarizability values.

One implementation of the technology can include a particle sensing apparatus including a tunable micro-laser, a mode splitting based whispering gallery mode micro-resonator and a coupling waveguide configured to transition the tunable laser in and out resonance modes. The combination can be embedded in a gas permeable encapsulation material. A photodetector can be configured to detect a laser signal output at an output port of the coupling waveguide and said photodetector configured to detect one or more of a resonance shift in a transmission spectrum and change in the mode pattern and said photo detector configured to output a signal indicative of the presence of a gas if one or more of a resonance shift in a transmission spectrum and change in the mode pattern is detected.

One implementation of the technology can include a particle sensing apparatus including a processor and a memory having data representative of plurality of speckle pattern changes for a plurality of common external perturbations and the memory can have a selection algorithm stored thereon. The technology can include a mode splitting based whispering gallery mode micro-resonator and a coupled tapered waveguide connected to a multimode fiber. A photodetector can be configured to detect an output signal at an output port of the coupled waveguide and said photodetector can be configured to detect a speckle pattern. The processor can be configured to process the selection algorithm to analyze a transmission spectrum of the detector output signal, thereby deriving a detected speckle patter change and selecting a matching speckle pattern change from the various speckle pattern changes.

On implementation of the technology can include a particle sensing apparatus including an ultra-narrow linewidth micro-laser, a mode-splitting based whispering gallery mode micro-resonator, and a coupled tapered waveguide configured to transition the ultra-narrow linewidth micro-laser laser in and out resonance modes. The whispering gallery mode micro-resonator can have a functionalized surface selected from one or more of an antibody bound on the surface, where said antibody is configured to bind with an antigen and a chemical configured to bind with a molecule. A photodetector can be configured to detect an output signal at an output port of the coupled waveguide and said photodetector configured to detect a frequency shift indicative of change in refractive index due to the functionalized surface.

One implementation of the technology can include an opto-electronic board including a laser source, data-acquisition card/function, detectors, polarization controller that can be connected to optical resonators to form a compact/portable resonator system. Such a system can be used for various applications including the one noted above. Examples include portable sensors, compact optical filters, a reference to lock and stabilize a laser with broad linewidth, and a portable laser source. Through an analog to digital converter, wireless signals can be generated and received by consumer products, such as laptops and phones.

For each of the implementations herein, where a coupling waveguide is referred, any comparable coupling medium can be utilized including, fiber tip, tapered fiber, angled polished fiber and even a free space medium for coupling light to a resonator. Coupling efficiency with tapered fibers can reach values as high as 99%. However, achieving this coupling and maintaining it for long durations require active stabilization and precise alignment with nano-positioning systems, because coupling conditions are prone to environmental perturbations (e.g., air flow and mechanical vibrations). This significantly limits the practical use of fiber-taper-coupled WGMRs. Alternative to evanescent coupling techniques is fabricating asymmetric WGMRs such as spiral, stadium, ellipsoid, quadrupole and limaco. There are also studies with well-known symmetric WGMRs, such as microspheres, micro-disks and micro-toroids, where circular symmetry is lifted by introducing controlled deformations either after the WGMRs are fabricated or during lithographic patterning.

Free-space coupling into and directional emission from deformed/asymmetric resonators are possible due to the dynamic tunneling between the co-existing chaotic and regular WGM modes, which help the light to escape from or couple into the resonator along the direction of deformation. Coupling of free space light into such resonators still remains as a challenge, mostly because it relies significantly on precise alignment of the focused free-space light on the cavity edge along the direction of deformation, which require optical and mechanical systems with high angular and translational resolution. These unavoidably make the system bulky and difficult to move out of the lab environment. Moreover, with the exception of a few studies, such cavities suffer from significant Q degradation as the degree of deformation is increased.

The technology as disclosed herein can utilize in lieu of a traditional waveguide a coupling medium such as a system and method for interfacing an optical cavity resonator, including a Whispering Gallery Mode micro-resonator, and free space light with cavity enhanced Rayleigh scattering. A system and method to couple light into whispering gallery micro-cavities/micro-resonators is disclosed.

The technology as disclosed uses scatterer induced coupling to interface free space light to whispering gallery modes of a micro-cavity. The technology establishes an interface between the free space light and the WGMs of resonators. This interface is formed by directly depositing nano-scatterers or nano-particles onto the WGMR. As demonstrated by testing, each of the nano-particles deposited on the resonator surface effectively act as a nano-coupler to couple free space light into WGMs without additional bulk optical components and precise alignment processes. One test configuration disclosed herein demonstrates lasing in an Ytterbium (Yb3+) doped silica micro-toroid.

The nano-scale interface between the micro-scale WGMR and the free-space light field utilizes cavity-enhanced Rayleigh scattering. The hybrid micro-resonator-nanoparticle system, as disclosed, enables the collection of a large fraction of the scattered light into the cavity mode via Purcell enhancement, and has the ability to harvest even weak light fields. The rate of spontaneous emission depends partly on the environment of a light source. This means that by placing the light source in a special environment, the rate of spontaneous emission can be modified. There is an enhancement of spontaneous emission rates of atoms when they are matched in a resonant cavity, which can generally be referred to as the Purcell Effect.

The nano-coupler scheme as disclosed brings together and leverages on various fundamental elements, which can include the following. First, the coupling of an emitter to a cavity mode enhances its spontaneous emission rate by increasing the local density of the modes, implying that the emitter will emit mostly into the cavity modes and with a much faster rate than in a vacuum. This enhancement is proportional to Q/V and is known as a Purcell enhancement factor. Second, a subwavelength particle (i.e., the nano-coupler) can be treated as an oscillating dipole, with the dipole moment induced by the electric field of the incident light, radiating into the surrounding space (i.e., Rayleigh scattering).

For the micro-resonator, there is no difference between the light coming from an emitter placed in proximity to the micro-resonator and the light transmitted via scattering from a nanoparticle illuminated by a free-space incident light. Thus, Purcell enhancement should take place leading to collection of the weak scattered-light into the cavity of the WGMR. Third, when a nano-particle is placed in close proximity to a micro-resonator and the nano-particle interacts with the evanescent field of the micro-resonator, light scattering back into the WGM occurs and also to the free-space reservoir modes takes place. Here, the Purcell effect manifests itself again by enhancing the coupling of the scattered light back into the degenerate WGMs (i.e., over 95% of the scattered light is coupled back). Fourth, nano-scatterers placed on the micro-resonator disrupt, i.e. break, its rotational symmetry thus open a channel for coupling light in and out of WGMs.

In previous schemes, resonators are intentionally deformed to break circular symmetry to enable free-space coupling of carefully aligned focused light, which comes with bulky size and alignment issues that hinder the realization of compact WGMR applications. The technology as disclosed herein using nano-couplers based on cavity enhanced Rayleigh scattering from nano-scatterer(s) on resonator surface provides as system and method that addresses these issues. A whispering gallery micro-laser is demonstrated through testing, disclosed herein, by free-space optical pumping of an Ytterbium doped silica microtoroid via scatterers. This technology scheme will not only expand the range of applications enabled by WGMRs, but will also provide a possible route to integrate them into solar powered green photonics.

These and other advantageous features of the present invention will be in part apparent and in part pointed out herein below.

BRIEF DESCRIPTION OF THE DRAWINGS

For a better understanding of the present invention, reference may be made to the accompanying drawings in which:

FIG. 3 is an illustration of a mobile device utilized for monitoring a speckle pattern;

FIG. 5A is an illustration of micro-resonator based magnetometer;

FIGS. 6A, 6B, and 6D are an illustration of one implementation of the technology for microresonator based acoustic imaging;

FIGS. 7A and 7B and 7C are illustrations of another implementation of the technology, a micro-resonator based sensor for thermal imaging can be achieved;

Figure 1:
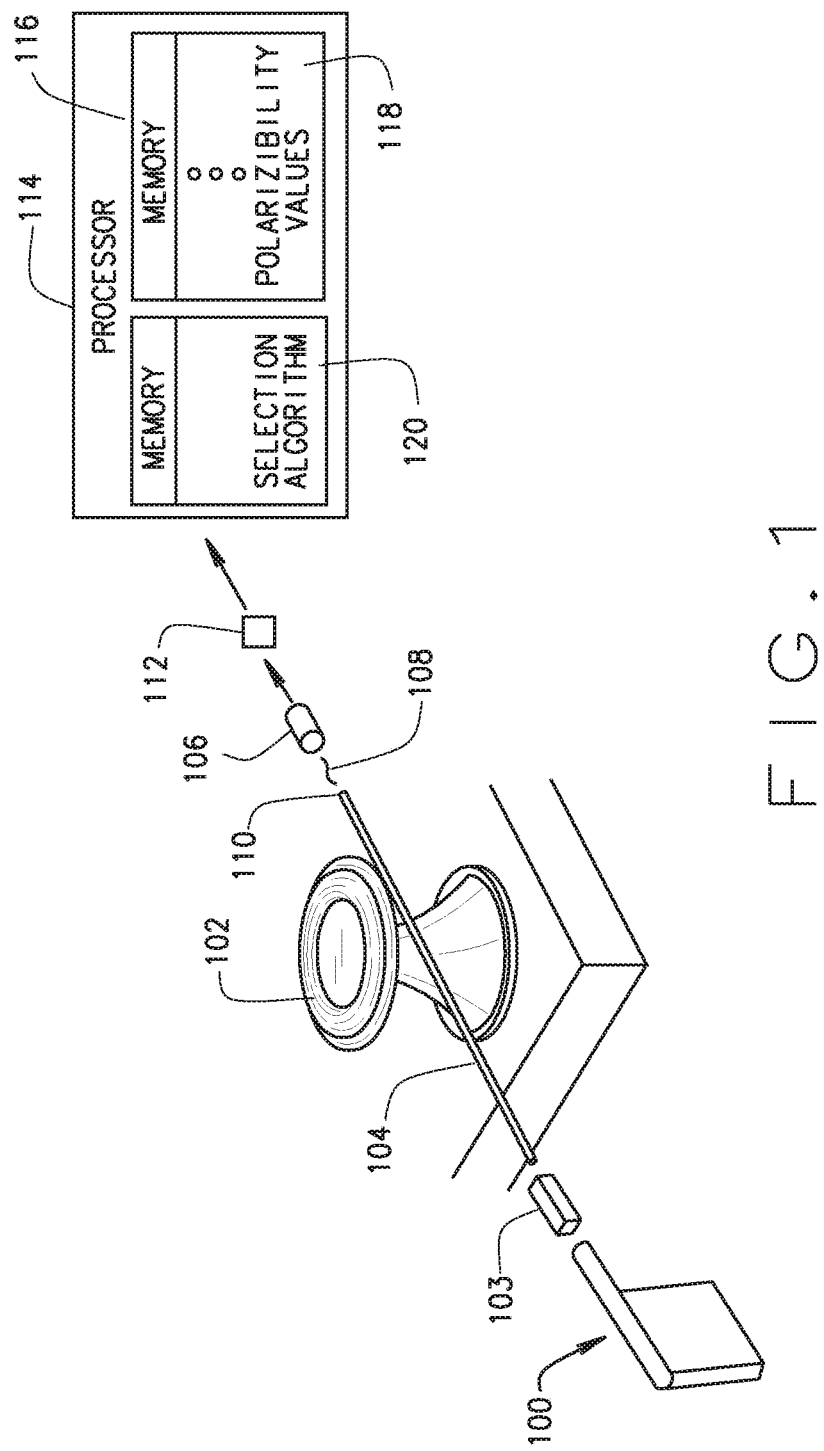
FIG. 1 is an illustration of a sensor for air quality measurement.

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DETAILED DESCRIPTION OF INVENTION

According to the embodiment(s) of the present invention, various views are illustrated in FIGS. 1-9 and like reference numerals are being used consistently throughout to refer to like and corresponding parts of the invention for all of the various views and figures of the drawing. Also, please note that the first digit(s) of the reference number for a given item or part of the invention should correspond to the Fig. number in which the item or part is first identified.

One implementation of the present technology comprising a micro-resonator and fiber taper based system teaches an apparatus and method for sensing particles. By way of background, particle binding splits a WGM into two spectrally shifted resonance modes, forming a self-referenced detection scheme. This technique provides superior noise suppression and enables extracting accurate size information in a single-shot measurement. Our technology as disclosed requires neither labelling of the particles nor information on their presence in the medium, providing an effective platform to study nanoparticles at single particle resolution.

Detecting single sized nanoparticles can be accomplished by leveraging mode-splitting, in a WGM resonator. Counting and sizing of individual nanoparticles as small as 30 nm in radius using scattering induced mode-splitting of a WGM in an ultra-high-Q microtoroid is possible. The demonstrated higher level of sensitivity and resolution can be attributed to two standing wave modes (SWM) formed after the adsorption of a particle, share the same resonator and experience the same noise. This allows a self-referencing detection system more immune to noise than the resonance shift based sensing schemes. The linewidths of the SWMs and the amount of mode splitting allow extracting the accurate size information regardless of where the particle is adsorbed, therefore enabling single-shot size measurement. The approach assists in realization of on-chip detection and sizing systems with single particle resolution.

After the first particle is deposited, SWMs are formed, which is confirmed by the mode-splitting (double resonances) in the transmission spectra. The consecutive particle depositions lead to changes in both the amount of splitting and the linewidths of the resonances. Discrete steps of various heights can be resolved indicating that individual nanoparticle adsorption events are resolved. Each adsorbed particle causes redistribution of previously established field; thus the height of each discrete step depends on the positions of the particles relative to the SWMs.

The underlying mechanism responsible for single-particle induced mode-splitting can is explained as follows: A nanoparticle in the evanescent field of WGMs acts as a light scatterer. Subsequently, a portion of the scattered light is lost to the environment creating an additional damping channel, while the rest couples back into the resonator and induces coupling between the two counter-propagating WGMs, whose degeneracy is lifted. This creates SWMs that are split in frequency. The SWMs redistribute themselves according to particle location: The symmetric mode (SM) locates the particle at the anti-node while the asymmetric mode (ASM) locates it at the node.

Consequently, the significantly perturbed SM experiences frequency shift and linewidth broadening. The strength of coupling g is quantified by the doublet splitting $g=\pi\delta$, where $\delta$ is the detuning of SM from ASM, and the additional linewidth broadening is quantified as $\Gamma_R=\pi|\gamma_1-\gamma_2|$ where $\gamma^1$ and $\gamma^2$ represent the linewidths of the split modes. In a regime where the particle is considerably smaller than light wavelength $\lambda$, the particle-WGM interaction induces a dipole moment in the particle. This dipole is represented by the polarizability $\alpha=4\pi R^3(\varepsilon_p-\varepsilon_m)/(\varepsilon_p+2\varepsilon_m)$ with $\varepsilon_p$ and $\varepsilon_m$ denoting dielectric permittivity's of the particle and the medium, respectively.

The parameters g and $\Gamma_R$ are given as $g=-\alpha f^2(r)w_C/2V_C$ and $\Gamma_R=-g\alpha w_C^3/3\pi v^3$ where $w_C$ is the angular resonant frequency, $f(r)$ designates normalized mode distribution, $V_C$ is the mode volume, and $v=c/\sqrt{\varepsilon_m}$ with c representing the speed of light. Consequently, we can derive the particle size from $\alpha=-(3\lambda^3/8\pi^2)(\Gamma_R/g)$ where $\Gamma_R$ and g can be measured from the transmission spectrum. Since the value of $\Gamma_R/g$ is independent of the particle position on the resonator, it gives the technique presented here a big advantage over schemes using resonance spectral shift, which is affected by particle positions. If $\varepsilon_S<\varepsilon_m$ ($\varepsilon_S>\varepsilon_m$), SM experiences a red (blue)-shift with respect to ASM.

For implementation of the technology, tunable lasers in the 670 nm and 1450 nm wavelength bands can be used. Their wavelengths can be linearly scanned around the resonance wavelength of the micro-resonator. The real-time transmission spectra can be obtained by a photodetector followed by an oscilloscope. This enables a real time monitoring of the transmission spectrum on the oscilloscope. The experimental set-up can consists of a differential mobility analyzer (DMA) system for size classification of nanoparticles, a nozzle for depositing nanoparticles onto the microtoroid, and a taper-fibre coupled resonator system. PLC: Polarization controller.

The details of the invention and various embodiments can be better understood by referring to the figures of the drawing. Referring to FIG. 1, an illustration of an air quality measurement system is illustrated. Miniature sensors can be utilized for air-quality measurements. The technology relates to a particle monitoring system on a chip with WGM resonators using mode splitting or frequency shift methods. Particle selectivity can be based on a polarization measurement which can be performed on each detected particle with single-shot measurement. An opto-electronic board including a laser source, data-acquisition card/function, detectors, polarization controller can be connected to an optical resonator to form a compact/portable resonator system. Such a system can be used for various applications. Examples include portable sensors, compact optical filters, a reference to lock and stabilize a laser with broad linewidth, and a portable laser source. Through an analog to digital converter, wireless signals can be generated and received by consumer products, such as laptops and phones.

A specific example is that polarizability values can be characterized in a series of experiments with common pollutants of air, and can form a database for each pollutant. In operation when a particle is detected and its polarizability is estimated, a code can use a mode selection algorithm to match the particle with one of the possible candidates in the database.

The system can include a tunable laser 100, a WGM resonator 102 and a coupling waveguide 104 to bring the laser in and out of the resonance modes. The tunable laser 100 can be a semiconductor laser (DFB or FP laser diodes), GaN or similar LED on-chip light source, or an on-chip WGM microlaser whose wavelength can be finely tuned by temperature control or by controlling the driving current. A polarization controller 103 can polarize the laser signal. A photoreceiver 106 (or a photodetector) can be used to detect the laser signal 108 at the output port 110 of the coupling waveguide 104. The output from the photoreceiver 106 is further processed 112 to extract the information of the light transmission from the resonator 102. A code can be used to analyze the transmission spectra to derive the polarizability values of the particles.

One implementation of the technology is a particle sensing apparatus, which includes a processor 114 and a memory 116 having data representative of plurality of polarizability values 118 for a plurality of common air pollutants. The memory can also have a selection algorithm 120 for analyzing output signals and finding matching data. The technology can include a tunable laser 100 and a mode-splitting based whispering gallery mode micro-resonator 102. The technology can include a coupled waveguide configured to transition the tunable laser in and out resonance modes.

A photodetector 106 can be included and can be configured to detect a laser signal output at an output port of the coupling waveguide and said photodetector can transmit a detector output signal representative of the detected laser signal output. The processor can be configured to process the selection algorithm to analyze a transmission spectrum of the detector output signal, thereby deriving a detected polarizability value and selecting a matching polarizability value from the plurality of polarizability values.

One implementation of the technology utilizing a micro-resonator and fiber taper based sensing system can include a portable sensor for volatile gas detection. Regarding one implementation of the technology, optical sensors using evanescent waves to interrogate the presence of analytes on the sensor surface or in the surrounding environment typically rely on detecting effective refractive index change. In order to detect very low concentration or minute amount of analytes using optical sensors, long waveguide lengths (exceeding cm) are typically required in order to accumulate a detectable phase shift.

This would also require significant amount of samples that may not be readily obtainable in many sensing applications. To address this problem, sensors based on optical micro-cavities can be used. Such sensors can offer a unique advantage by reducing the size of the device by orders of magnitude, without sacrificing the interaction length by virtue of the high quality (Q) factor resonances, thereby significantly reducing the amount of sample needed for the detection. The resonance effect provides an effective long interaction length for the sensor to achieve sufficient sensitivity.

Also typical bio-sensing experiment requires that the devices can handle aqueous analytes. Therefore fluidic handling capability can be a part of the sensor platform. High quality-factor microsphere cavities using Whispering gallery mode (WGM) resonances have been demonstrated to respond to a monolayer of protein adsorption, however integration with fluidic system is very challenging and typically requires fluidic chambers much larger than the active device element.

Figure 2:
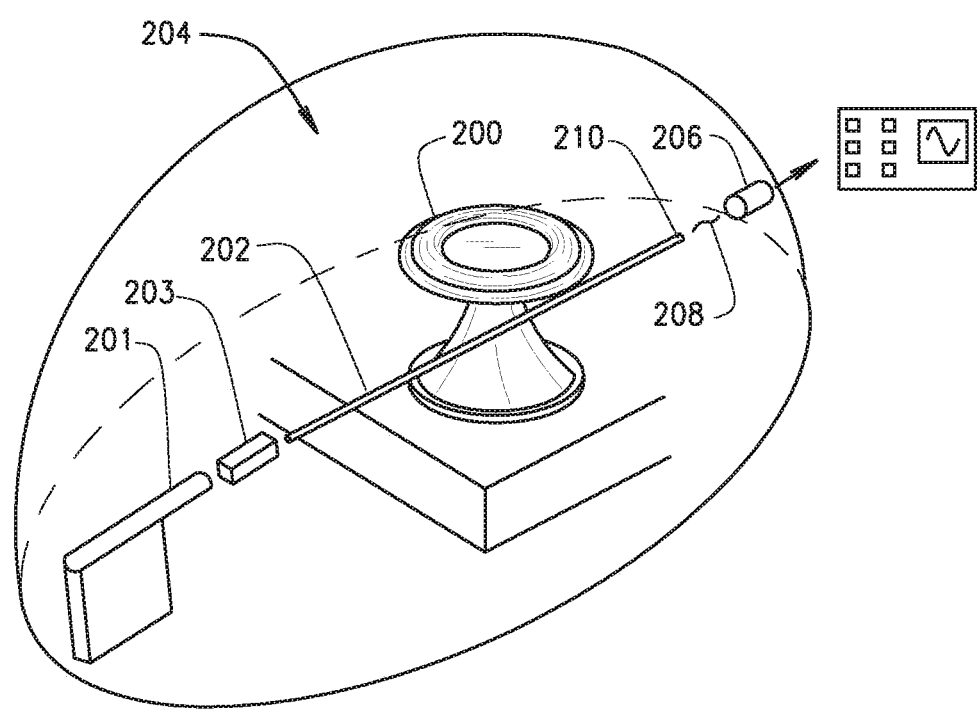
FIG. 2 is an illustration of a sensor for detection of gas.
Figure 4A:
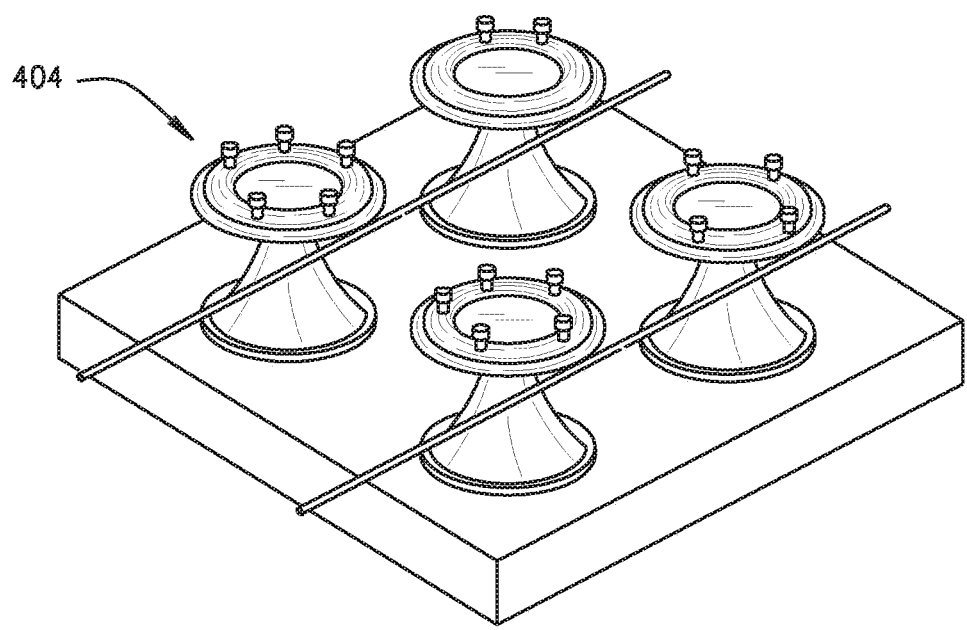
FIGS. 4A, 4B, 4C and 4D are illustrations of systems utilizing a multicolor ultra-narrow linewidth laser.
Figure 4B:
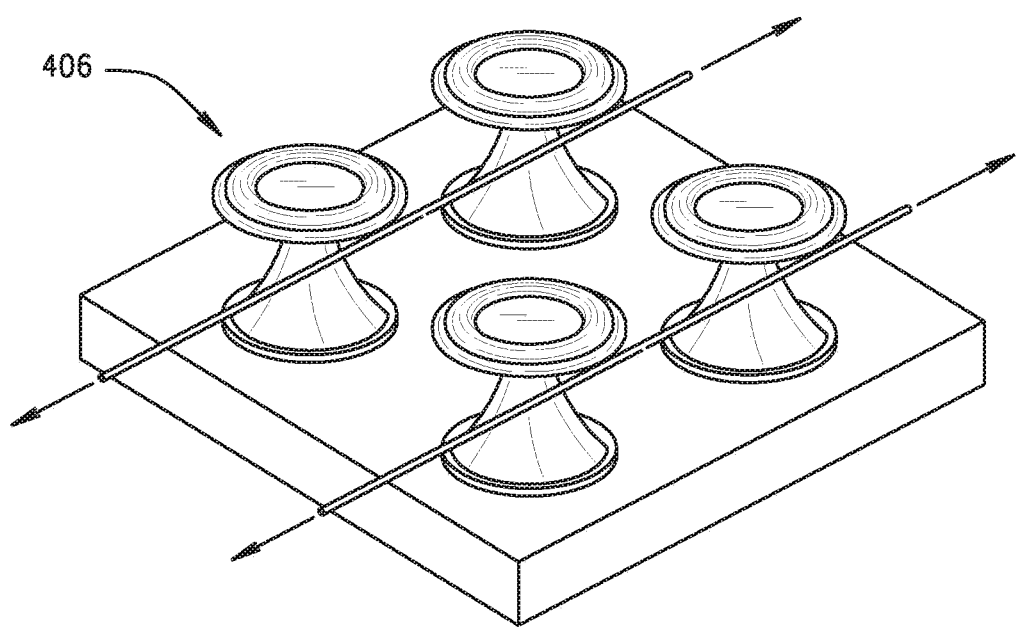
Figure 4C:
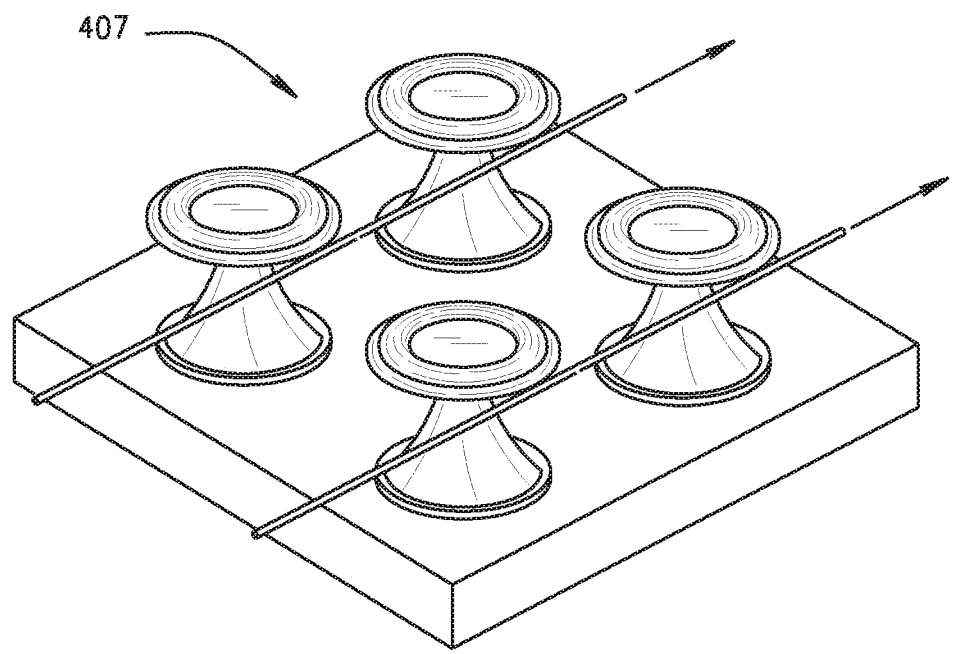
Figure 4D:
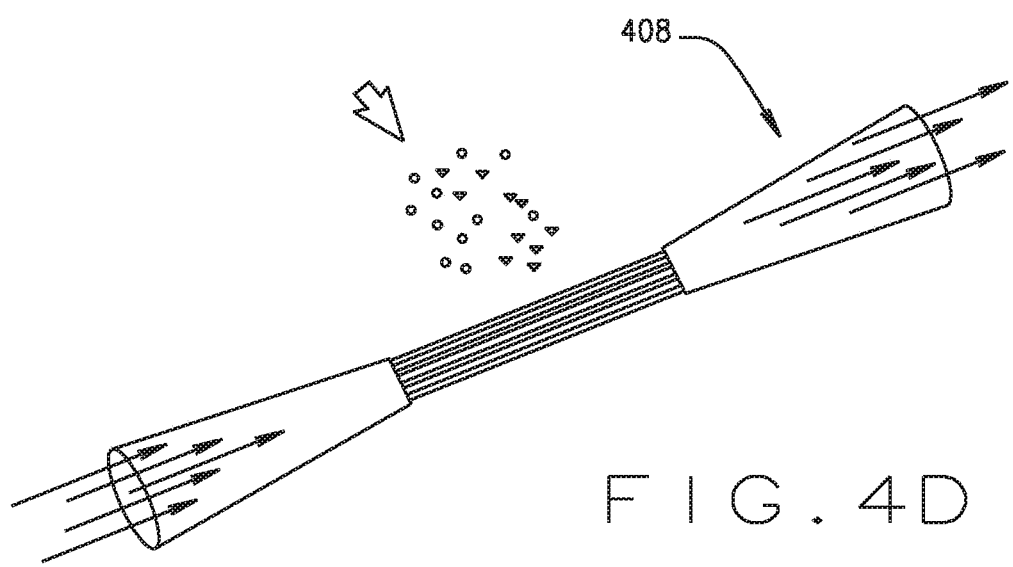

With the above introduction, referring to FIG. 2, one implementation of the technology can include a resonator 200 and the coupling waveguide 202 that can be embedded into a packaging material 204 (such as Polydimethylsiloxane (PDMS), zeolite (microporous aluminosilicate minerals), etc) through which certain volatile gas (fluorobenzene, methyl chloride, butane, Heptene, CO, radon, and natural gas (hydrogen sulfide, mercaptan), explosives (TNT, nitrate), etc) can permeate. A polarizer 203 can polarize the laser signal. Once the gas penetrates through the packaging materials 204 and approaches the resonator 200, the effective refractive index experienced by light in the resonant mode changes. Subsequently a resonance shift in the transmission spectrum or a change in the mode pattern of the resonator will be observed, which indicates the presence of the gas. The portable sensors can appear in different forms, such as wrist band, fiber stem, sensor network connected by optical fibers. The system may also have a particle or gas collection and purging unit, which will sample the air and then blow it onto the resonator.

One implementation of the technology is a particle sensing apparatus includes a tunable micro-laser 201 and a mode splitting based whispering gallery mode micro-resonator 200 and a coupling waveguide 202 configured to transition the tunable laser 201 in and out of resonance modes. All of which can be embedded in a gas permeable encapsulation material 204, such as for example PDMS or zeolite.

A photodetector 206 can be included that is configured to detect a laser signal output 208 at an output port 210 of the coupling waveguide 202 and said photodetector 206 configured to detect one or more of a resonance shift in a transmission spectrum and change in the mode pattern and said photo detector configured to output a signal indicative of the presence of a gas if one or more of a resonance shift in a transmission spectrum and change in the mode pattern is detected.

One implementation of the technology utilizing a microresonator and fiber taper based sensing system can include a mobile device based monitoring of fiber speckle patterns for portable sensors to image resonator mode patterns with a mobile device's camera for sensing. Speckle patterns and the mode patterns are highly sensitive to external perturbations. In a multimode fiber spectrometer, the interference between the guided modes creates a wavelength-dependent speckle pattern, providing the required spectral to-spatial mapping. The contrast of this speckle pattern is found to depend on the spectral width and shape of the optical source, allowing the use of contrast as a measure of the laser linewidth. As opposed to using only the statistical property of the speckle such as the contrast, one implementation of the technology demonstrates that by recording the entire speckle patterns at different wavelengths, a multimode fiber can be used.

For example, in one implementation of the technology the resonance shift of a resonator due to a binding analyte or change of refractive index can be directly monitored by monitoring the changes in the mode pattern. Similarly speckle patterns formed in tapered waveguides (i.e., fiber tapers processed from single mode fibers) connected to a multimode fiber can change due to any external perturbation, such as binding analyte, refractive change, pressure variations, temperature fluctuation, etc. These changes in the speckle patterns can be directly monitored by CMOS cameras 314 available in smart phones.

An adapter can be attached to the phone for stabilization of the system and for making use of the imaging function of the smart phone. There can be an app which will process the images taken to provide information on the speckle or mode pattern changes and relate to the parameter of interests (resonance shift, the correlation time, contrast of speckle patterns).

Referring to FIG. 3, one implementation of the technology is a particle sensing apparatus including a processor 300 and a memory 302 having stored thereon data representative of plurality of speckle pattern changes 304 for a plurality of common external perturbations. The memory 302 can have stored thereon a selection algorithm 306. The technology can include a mode splitting based whispering gallery mode micro-resonator 308 and a coupled tapered waveguide 310 connected to a multimode fiber 312. A photodetector 314 can be configured to detect an output signal 316 at an output port 318 of the coupled waveguide and said photodetector configured to detect a speckle pattern. A laser 301 through a polarization controller 303 can drive the signal.

The processor can be configured to process the selection algorithm to analyze a transmission spectrum of the detector output signal, thereby deriving a detected speckle patter change and selecting a matching speckle patter change from the plurality of speckle pattern changes.

Referring to FIGS. 4A, 4B, 4C, and 4D, one implementation of the technology is a particle sensing apparatus including, an on-chip multi-color ultra-narrow linewidth laser for spectroscopy, holography, sensing and imaging. Multiple micro-lasers emitting light at different wavelengths are shown. The optical gain used to generate lasing signals can come from rare-earth ions, nonlinear effects, such as stimulated Raman scattering process, quantum dots, and dyes. By tailoring the composition of the gain materials, we can adjust the lasing wavelength, i.e., color, of the micro-lasers.

A lasing signal with ultra-narrow linewidth can be generated when sufficient pump light is coupled into the microresonator. The ultra-narrow-linewidth lasers can serve as light sources for spectroscopy, holography and imaging. These multi-color ultra-narrow linewidth lasers can also serve as source light for passive resonators, which will be multifunctional miniature sensors for temperature, pressure, humidity, gas and particle sensing.

They can also be used as multifunctional miniature sensors because the frequency of the lasing signal shifts due to changes in the local environment, such as temperature changes, pressure fluctuation, humidity variations, and analyte binding, etc. The aforementioned changes in the environments can trigger changes in the refractive index of the lasing mode. The working principle of the microlaser based sensor relies on the fact that any disturbance that can trigger changes in the effective refractive index of the lasing mode is manifested as frequency shift in the lasing signal, which can be measured as sensing signal indicating changes in the environment.

For biosensing applications, selectivity can be achieved by functionalization of the resonator surface with antibodies that can bind with targeting antigens or chemicals that can capture targeting molecules. For one implementation of the technology multiple micro-resonators can be fabricated on the same chip 404. The surface of each resonator can be functionalized with particular antibodies to capture specific antigens. The presence of a specific antigen in the test solution will be indicated by a change in the transmission spectrum of the micro-resonator triggered by a binding event between the antigen and antibody which is already bound to the resonator surface. The surface of each resonator can also be functionalized with particular chemicals that are sensitive to variation in temperature, humidity, or pressure of the environments. The change in the aforementioned conditions can trigger a resonance shift in the transmission spectrum of a particular resonator, which is functionalized with the chemicals that are sensitive to variation in the condition that induce the change For yet another implementation of the technology, multiple micro-resonators and micro-lasers can be mixed on the same chip 406. In such a system, the ultra-narrow linewidth light generated from the micro-lasers serve as light sources for the passive micro-resonators 407 for sensing applications. Also, multiple fiber tapers can be bundled together 408 to form a multi-function sensing system. Each fiber taper can be functionalized with particular chemicals that can bind with specific molecules or proteins for bio/chemical sensing applications. The fiber tapers can also be functionalized with particular chemicals that are sensitive to variation in temperature, humidity, or pressure of the environments. The light signal transmitted through the fiber tapers will be the sensing signal analyzed by a code to trace back changes in the environments.

The linewidth of a laser determines its temporal coherence. The narrower the linewidth the longer the temporal coherence. Temporal coherence is a measure of the ability of the light to perform interference, thus longer coherence time is crucial for a number of applications, including holography, interferometry, Doppler velocimetry and ranging, heterodyne mixing.

In Doppler velocimetry, a laser light shines on a moving object and the reflected light is detected. The change in the frequency of the incident and the detected light is the Doppler shift which is dependent on the velocity of the target. If the incident light has poor coherence, the detected light will have a broader spectrum, limiting the accuracy of measuring the Doppler velocity. Thus, the narrower the linewidth, the longer the coherence length and therefore the better the accuracy of measurement.

In holography, the temporal coherence length (the linewidth of the laser) determines the maximum depth of the object in a reflection hologram. Holography is based on the interference between light beams. Thus long coherence length enables taking holograms of large bodies, which require greater depth of field. Both the light reflected from the near part of the body, and the light reflected from the far part of the body, will still be coherent with the reference beam.

Narrow linewidth lasers are also needed in coherent and heterodyne detection where light reflected off a target or emitted from a source is mixed with light from another laser to create a fringe pattern. If the laser has narrow linewidth the photons from the laser will maintain fixed frequency and phase relationship for the time needed to hit the target and return in order to have proper contrast in the fringe pattern.

Microcavity lasers that we fabricate have ultra-narrow linewidths which mean that the lasers have ultra-long coherence lengths. By suitably choosing the dopant, we can obtain multicolor emission from a single microcavity (2 or 3 different colors are within reach in our lab). For example, combined doping of thulium, neodymium and erbium together with a large bandwidth LED pump, may enable lasing in the blue, red, green as well as infrared frequencies. These emissions are collected by a fiber and directed to the object, medium or target surface to be recorded. The interference patterns of the reflected light from the target and the reference light can be detected by a CCD or CMOS camera simultaneously for each color and further processed to reconstruct the images on a PC.

In a different system, a series of microcavities each doped with a different rare-earth-ion or gain medium can be used. Emissions from each of the microcavity will have a different color. These can be combined in a fiber, divided into a reference and object beam using fiber couplers. The object beam is then carried in the fiber waveguide to illuminate a target surface. The light reflected from the target and that of the reference are recorded then on a CCD and processed to reconstruct image.

Such a system with the availability of multiple colors of laser emission with ultra-narrow linewidths will help to get better resolution and imaging as well as improved depth. The system will be portable and can be implemented/installed in scenarios where power and space budgets are limited, and better resolution and maximum depth of object are required.

Based on the above, one of the implementation of the technology is a particle sensing apparatus including an ultra-narrow linewidth micro-laser 410. The technology can also include a mode-splitting based whispering gallery mode micro-resonator 412 and a coupled tapered waveguide 414 configured to transition the ultra-narrow linewidth micro-laser in and out of resonance modes. The whispering gallery mode micro-resonator can have a functionalized surface 416 selected from one or more of an antibody bound on the surface. The antibody can configured to bind with an antigen and a chemical configured to bind with a molecule. A photodetector 418 can be configured to detect an output signal 420 at an output port 422 of the coupled waveguide and said photodetector configured to detect a frequency shift indicative of change in refractive index due to the functionalized surface.

The particle sensing apparatus can include the functionalized surface and can be selected from one or more of a chemical that is sensitive to a variation in temperature, humidity, or pressure. The coupled tapered waveguide surface can be functionalized with a waveguide chemical configured for one or more of binding to a molecule, sensing variation in temperature, sensing a variation in humidity and sensing a variation in pressure. A dopant can also be applied to the surface of a micro-resonator thereby configured to enable lasing in multiple colors.

Such a system will also enable to extract multiple parameters about the sensing area. For example, a hologram recording the sample undergoing concentration and temperature changes can provide both the concentration and temperature variations of the sample if multiple colors are used.

Figure 5B:
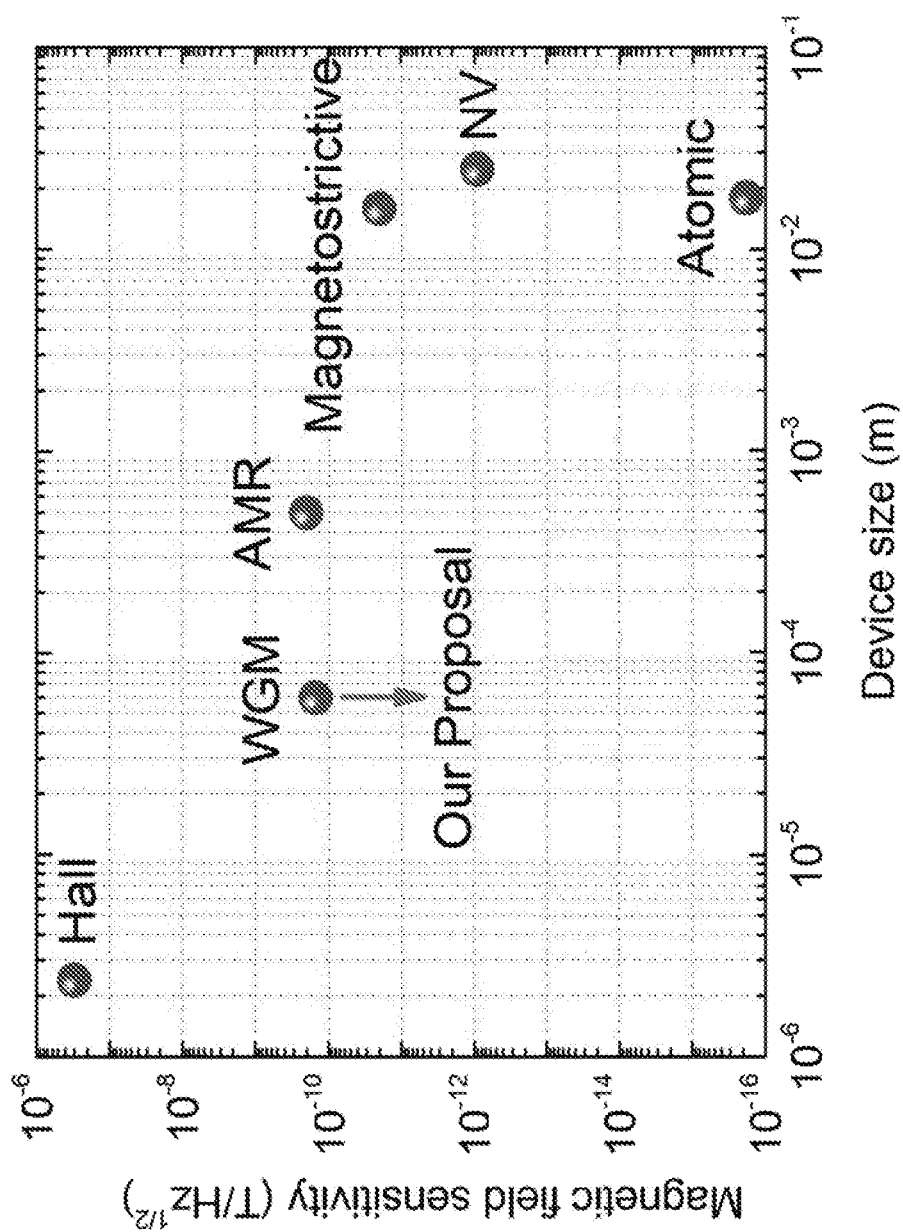
FIG. 5B is a graphical illustration of the magnetic sensing.

Various wave sensors can also be accomplished utilizing the technology as disclosed including IR, magnetic, radiation and acoustic waves. FIG. 5 illustrates a WGM microresonator based magnetometer 500 using a piece of magnetic sensitive material, such as for example Terfenol-D 502, can be fabricated on the silicon substrate of a microresonator 504. A laser 503 can drive the micro-resonator through a polarizer controller 501. The piece of Terfenol-D or other magnetic material can expand and contract or otherwise react based on the presence of a magnetic field 506 generated by a magnetic field generator 505. Other types of magnetic sensitive material that can be used are Terbium and Neodymium. A change in the spectral transmission can be received by a spectrum analyzer 508 for analysis. In addition to the magnetic material being adhered externally to the top of the micro-resonator, the magnetic material can be applied by doping the micro-resonator with the magnetic material or the entire micro-resonator can be constructed of the material. With no magnetic field the transmission is a Lorentzian dip and a doublet formation under the magnetic field.

Figure 8A:
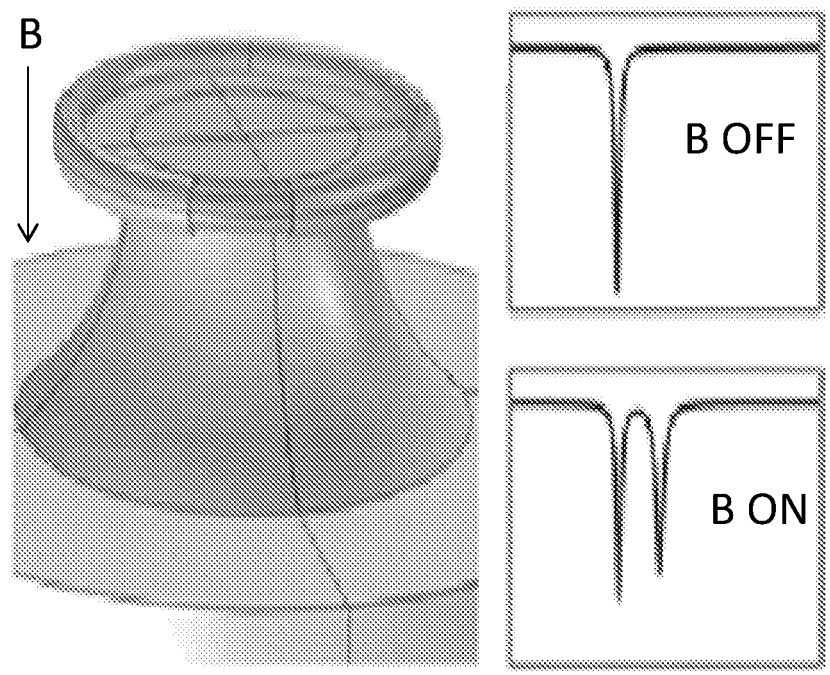
FIGS. 8A and 8B illustrate magnetic field sensitivity versus sensor size.
Figure 8B:
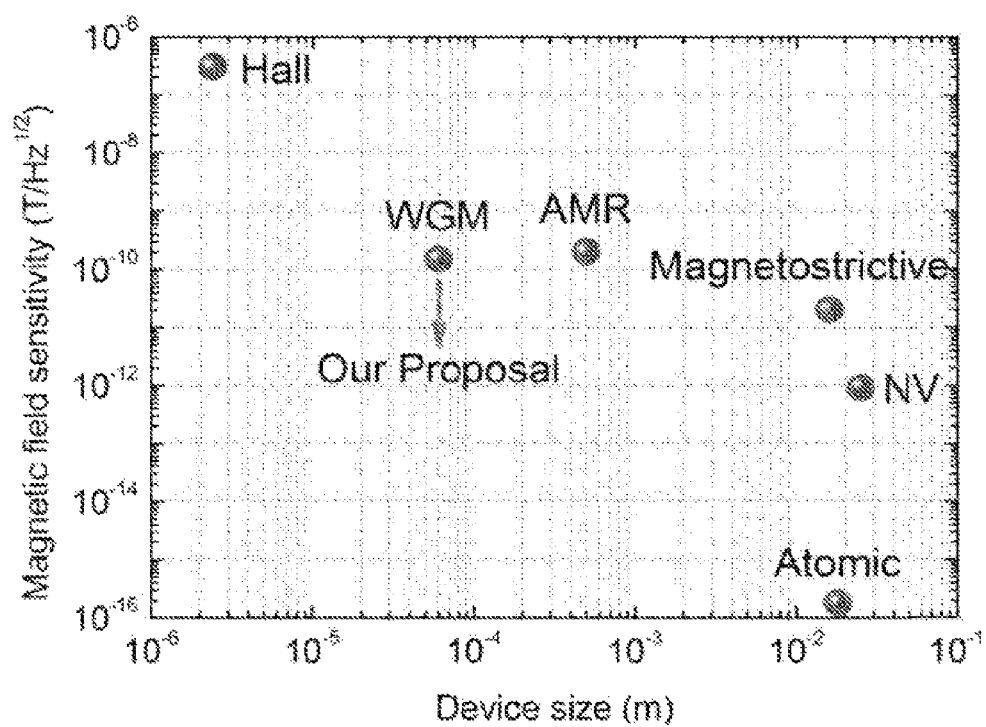

Referring to FIGS. 8A and 8B, as previously discussed, microtoroid whispering gallery mode resonators (WGMRs) are one of the most exquisite platforms for enhancement of light-matter interactions. Strengthening the interaction of a variety of materials with light leads to various applications. With WGMRs, rare earth ions such as $Er^{3+}$ and $Yb^{3+}$ yield ultralow threshold microlasers, Rayleigh scatterers provide single particle sensitivity and even optically inactive materials like silica can generate a sub-milliwatt Raman laser[1,2]. Therefore, it is only instinctive to expect highest yield from a magneto-optic material when incorporated within a microtoroid WGMR. Here the technology as disclosed presents an on-chip microtoroid resonator coated with a $Tb^{3+}$ doped sol-gel layer to perform magnetic-field sensing. Terbium doping in silica is a well established method for creating magneto-optic effect based optical isolators and other devices. Although other magneto-optic materials such as garnets or polymers provide larger Verdet constants, they are inadequate for integration and design as stand-alone photonic devices however silica microtoroid WGMRs are suitable devices for coating with polymers or doping with $Tb^{3+}$ ions as indicated in the previous section. Since the magneto-optic effect is dependent on the optical path length, high quality factor WGMRs with finesses of 10,000 are superior to the existing technologies.

By dip coating microtoroids in an $Er^{3+}$ doped sol-gel solution, annealing for 10 hours and later reflowing with a $CO_2$ laser an ultra-low threshold (34 µW) Erbium microlaser was demonstrated. This result shows that with the exact same procedure, we can create Terbium doped sol-gel coated silica microtoroid WGMRs to achieve ultra-high magnetic sensitivities. With silica toroidal WGMRs one is not restricted with the use of silica and silicon. As demonstrated coating of silica WGMRs with polydimethylsiloxane (PDMS) for compensating thermal refraction in silica where the quality factors were only decreased from $10^7$ to $10^6$. Recently, with regioregular polyalkylthiophenes Verdet constants as high as $10^5$ (°/Tm) have been reported by Gangopadhyay[6] et al. Combining the compatibility of silica with polymer coatings and the developments in magneto-optic polymers, we design a magnetic sensor with capabilities eclipsing that of the existing optical magnetic sensors. From sensitivity, stability, reliability to compact device design and cost our device outperforms the state of the art technologies.

The magnetic sensing theory is based on gyrotropic mode splitting. Mode splitting in WGM resonators has been demonstrated as a single nanoparticle sensing method. According to this method, a nanoparticle adsorbed on the surface of a silica microtoroid WGMR lifts the degeneracy of the modes propagating in the opposite directions. The degeneracy breaking then leads to creation of standing wave modes and from there the nanoparticle size or refractive index can be obtained. The method for detecting magnetic fields relies on a similar approach. The degeneracy lifting is achieved by asymmetric changes in the refractive index of the magneto-optic material instead of a nanoparticle adsorbing on the surface. With a known Verdet constant, the method predicts the magnetic fields causing the gyrotropic splitting.

A Terbium doped silica sol-gel or a magneto-optic polymer coated silica microtoroid under uniform magnetic field will have an anisotropic permittivity tensor with non-diagonal terms $$\varepsilon = \begin{matrix} \varepsilon & ig & 0 \\ -ig & \varepsilon & 0 \\ 0 & 0 & \varepsilon \end{matrix}$$

where $\varepsilon$ is the permittivity of silica without magnetic field and g is the gyrotropic constant from Terbium doped silica or a magneto-optic polymer, which can be expressed as $$g = \frac{V\lambda n |B_{ext}|}{180°}$$

where V is the Verdet constant, $\lambda$ is the wavelength, n is the refractive index and $B_{ext}$ is the external magnetic field. With $B_{ext}$, the refractive index of the coated layer is modified and the effective refractive index for CW and CCW modes can be found by $n_{eff}=(n^2 \pm g)^{1/2}$. Sensitivity to changes in the refractive index of a medium that experiences the evanescent field of a WGMR is on the order of several 100 nm per refractive index unit (RIU). A WGM at 1500 nm band with a quality factor of $10^8$ will then be able to sense changes in the refractive index as small as $10^{-7}$. A magneto-optic coating with a Verdet constant of $10^3$ (°/Tm) on a silica WGMR, will also detection of magnetic fields as small as several pT. Note that, the magneto-optic effect here is a non-reciprocal phase shift which essentially can be realized as a frequency splitting between the clockwise (CW) and the counterclockwise (CCW) propagating modes due to the asymmetric permittivity of the medium. Once the degeneracy of the two modes is lifted, the CW and CCW modes couple and create a standing wave mode which embodies as a doublet in the transmission. The amount of splitting then is a function of the gyrotropic constant g and therefore the magnetic field that needs to be sensed. Although theorized, a gyrotropic mode splitting in WGM resonators have not been demonstrated so far. The device will be the first demonstration of gyrotropic mode splitting in WGMRs. Eliminating the thermal and mechanical noises which hinder the practicality of WGMRs by a self-referencing mode splitting method, our device will not only achieve an unprecedented sensitivity, but will also be reliable and stable. The device fabrication is only based on well-established technologies which will allow mass production of cost-effective and micro-scale magnetic sensors to be used in aerospace applications.

Further, it should be noted that when radiation from photons impinge on a surface, the momentum of photons change, which generates radiation pressure applied to the surface. This process can be explained by newton's Second and Third Law. Therefore, by coupling magnetic-field-induced strain of a magnetostrictive material to the mechanical vibration of an opto-mechanical micro-resonator, a resonator opto-mechanical magnetometer can be achieved.

Ultrahigh-sensitive magnetic field sensors are indispensable components for a wide range of applications, such as geology, archaeology, mineral exploration, medicine, defense, and aerospace. Taking aerospace for example, magnetometers are essential elements for obtaining spacecraft attitude coordinates by measuring the geomagnetic field; another example is satellites to study magnetic space explosions. The current state-of-the-art of ultrahigh-sensitive magnetometry is achieved by Superconducting Quantum Interference Devices (SQUIDs), which enable detection of single electron spin. However, operation at liquid-He atmosphere temperatures limits the real applications especially for aerospace. Magnetometers capable of room temperature operation offer significant advantages both in terms of operational costs and range of applications. The state-of-the-art is atomic magnetometers which achieve impressive sensitivities as low as 160 pT $Hz^{-1/2}$. Recently, rapid progress has also been developed on NV center based magnetometers. Sensitivities as low as 0.9 pT $Hz^{-1/2}$ has been achieved. However, the atomic magnetometers remain limited to centimeter size scales. On the other hand, HV center based magnetometers need a centimeter-size test system, which hinders the potential application in biology, medicine, and especially aerospace.

Due to the $1/r^3$ decay of magnetic dipolar fields, sensor size is a critical parameter to further improve the sensitivity of sub-femto-tesla magnetometers. Thus, a number of technologies have developed to achieve a higher sensitivity together with a smaller sensor size. Here, we briefly review the magnetic field sensitivities and sizes for various available sensors at room temperature, as shown in FIG. 8B. Among them, the whispering gallery mode (WGM) micro-cavity based optomechanical magnetometer operating in the 100 pT range is a probable candidate for the aerospace application to balance the size (including the coupling system) and the sensitivity. The optical WGM micro-cavitybased magnetometer is particularly suited for space and aeronautics applications for the following reasons. First the micron-dimension size together with pT Hz$^{-1/2}$ sensitivity is the best choice for the aerospace application, which can be seen clearly from FIG. 8B. On the other hand, the optical magnetometer offers the intrinsic advantage of low electromagnetic interference and thus isolates the electronic measurement noise comparing with electronic magnetometers considering the complex electromagnetic environment in outer space. However, the sensitivity of the WGM based optomechanical magnetostrictive magnetometer is still far away from the state-of-art, limited by the poor coupling of the magnetostrictive material (Terfenol-D) to the optical cavity (microtoroid) due to the space separation of the magnetostrictive material and the cavity.

Here, the technology as disclosed presents to use high-Q WGM resonators coated with terbium doped sol-gel layer that is responsive to magnetic field for magnetic sensing. The presented use has several advantages over WGM optomechanical based magnetometer. First, the presented use is based on the Faraday Effect, which is more reliability than magnetostrictive magnetometer, since the latter is also sensitive to the mechanical vibration and temperature drift, but the former is not. Second, the sensitivity of terbium doped WGM based magnetometer will be much higher than optomechanical magnetostrictive magnetometer because of not only the highest Verdet constants in terbium doped silica glasses but also the higher coupling between the terbium and cavity mode. Third, the fabrication method (spin coating) of our devices is much more repeatable and suitable for flow production. Last but not least, the extreme temperature drift in outer space can be compensated by suitable polymer coating in our case.

FIG. 8B illustrates magnetic field sensitivity versus sensor size (including coupling system) for various available sensor techniques (blue points) at room-temperature, including Hall-magnetometers (Hall), whispering gallery mode resonator based magnetometers (WGM), anisotropic magnetoresistance magnetometers (AMR), magnetostrictive magnetometers, NV center based magnetometers (NV), and atomic magnetometers (atomic).

In one implementation a the technology, a microresonator based photo acoustic imaging can be achieved. A microresonator 600 and coupled waveguide 602 can be place in water 604 or other acoustically comparable medium. An ultrasound transducer 606 can coupled to the medium 604 to induce an acoustic signal 608. The micro-resonator can be powered by a laser 610 through a polarization controller 612. The acoustic signal can be detected by a signal analyzer 614 in the optical resonance amplitude 616 of the micro-resonator.

Referring to FIGS. 7A and 7B and 7C, in yet another implementation of the technology, a micro-resonator based sensor for thermal imaging can be achieved. Through thereto-optic effect, a resonant wavelength (frequency) shifts when a thermally isolated resonator is illuminated by infrared radiation, which can be used for thermal imaging. Thermal relaxation time measurements 706 reveal that the smaller pillar size leads to a longer thermal relaxation time.

Referring to FIG. 7A, an illustration of a spectral shift is provided. A single resonance mode experiences red-shift upon IR irradiation. Referring to FIG. 7B, an illustration of mode splitting is provided. Single resonance mode splits into two due to intra-cavity back scattering from an IR responsive scattering center (purple circle). IR irradiation leads to not only spectral shift in the split modes but also a change in mode splitting.

Techniques in thermal sensing using resonators (e.g., mechanical resonators including cantilevers, plasmonic devices, optical resonators) relies on monitoring the spectral shift of a single resonance mode (See FIG. 7A) either directly by scanning a tunable laser line around a resonance wavelength or indirectly by measuring the changes in the transmitted power of a laser operating at the 3-dB point of the resonance. Lack of a reference in this approach hinders discriminating the perturbations of interest, such as IR induced thermal changes, from irrelevant local or global interfering perturbations, because spectral shift of a single resonance is also very sensitive to laser intensity and frequency fluctuations detector noise, and other environmental disturbances such as dust or nano-scale objects entering the resonator mode volume. Thus, detecting a resonance shift does not necessarily imply a thermal signal. Consequently, one cannot discriminate spectral shifts induced by IR irradiation from that induced by non-IR sources, such as thermal fluctuations of the background.

However, the technology as disclosed introduces mode splitting in active and passive WGM optical resonators as a novel self-referencing technique for detecting perturbations in or in close proximity to the resonator. In this approach, a single resonance mode splits into two spectrally shifted resonance modes with different resonance linewidths (See FIG. 7B). The required information is then extracted by comparing the spectral properties of the split modes. Since both of the split modes reside in the same resonator, they are affected similarly by common noises such as those originated from laser intensity and frequency fluctuations, coupling distance fluctuations or any jitter or noise that affects the resonator uniformly. This helps to minimize, if not eliminate, the effect of interfering perturbations by using one mode as a reference for the other. Therefore, due to its self-referencing feature, the mode splitting approach generates more sensitive and reliable sensing signals. On the other hand, the splitting signal is very sensitive to even trace amount of changes in the optical, physical or chemical properties of the scatterers in the resonator mode volume. This provides a way to monitor IR radiation using IR sensitive and responsive scatterers within the mode volume.

Referring to FIGS. 9A, 9B, 9C and 9D, Whispering gallery mode (WGM) resonators have been used to achieve high sensitivity single nanoparticle/molecule sensors. But most experiments are based on monitoring the changes in resonance spectra induced by the particle/molecule. A tunable laser is thus required to generate the spectrum and achieve the real-time operation. Although very good sensitivity and particle sizing is achieved, these requirements place significant hindrance on miniaturizing the system and lowering the cost. Here we describe a technique that only relies on power measurements. This method monitors the power change of resonance enhanced reflection by nanoparticles in a microresonator. Although the basic idea of probing the reflected light has been previously reported in literatures through the configuration of add-drop filter, experiments on real-time detection have not been demonstrated. In this proof-of principle experiment we used a tunable laser, however methods are available to replace it with a laser diode which can be thermally locked to a resonance.

Figure 9A:
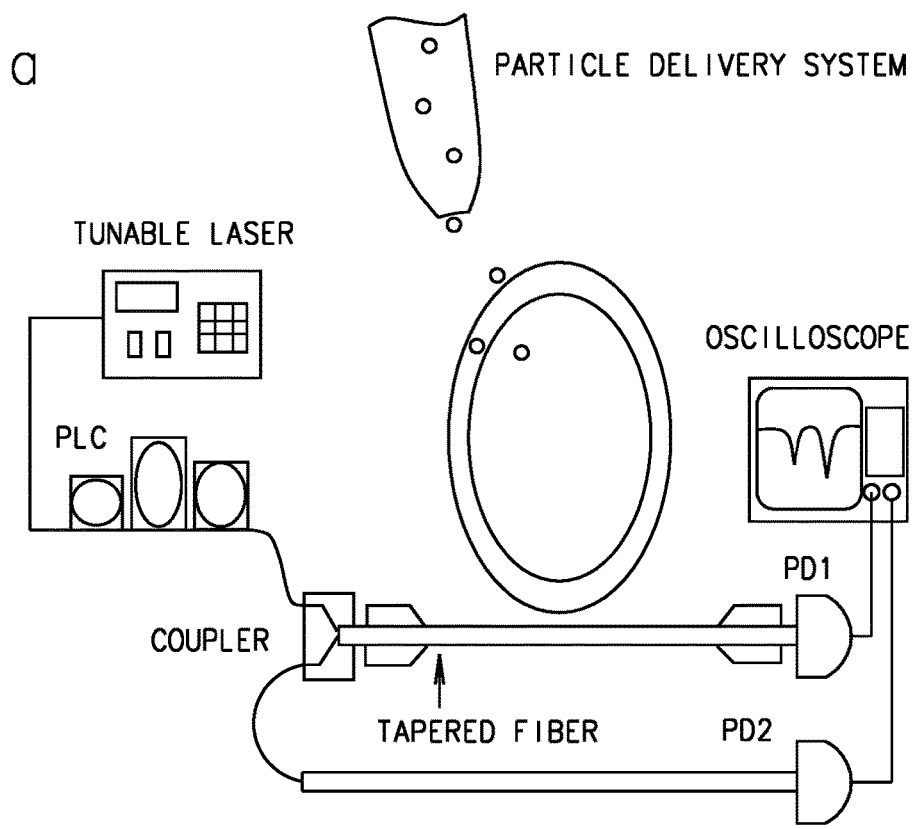
FIGS. 9A, 9B, 9C, and 9D are illustrations of Whispering gallery mode (WGM) resonators used to achieve high sensitivity single nanoparticle/molecule sensors.

One may even use a broadband light source, such as LED, since no wavelength information is needed in the scheme. Scattering centers on a microresonator such as nanoparticles can induce mode splitting. It effectively couples the two counter propagating modes. Therefore the power in the original forward propagating direction is coupled into the backward direction. It allows us to receive light in the back-reflection port. FIG. 9A describes the experiment setup. Initially when there are no particles on the microtoroid, only the counter clock-wise (CCW) mode exists and PD2 doesn't receive light. When particles are adsorbed onto the surfaces of the microtoroid, they scatter light into the clock-wise (CW) mode and subsequently the light is coupled back to the fiber taper in the back-reflection direction. This process can be monitored by PD2 real-time.

Figure 9B:
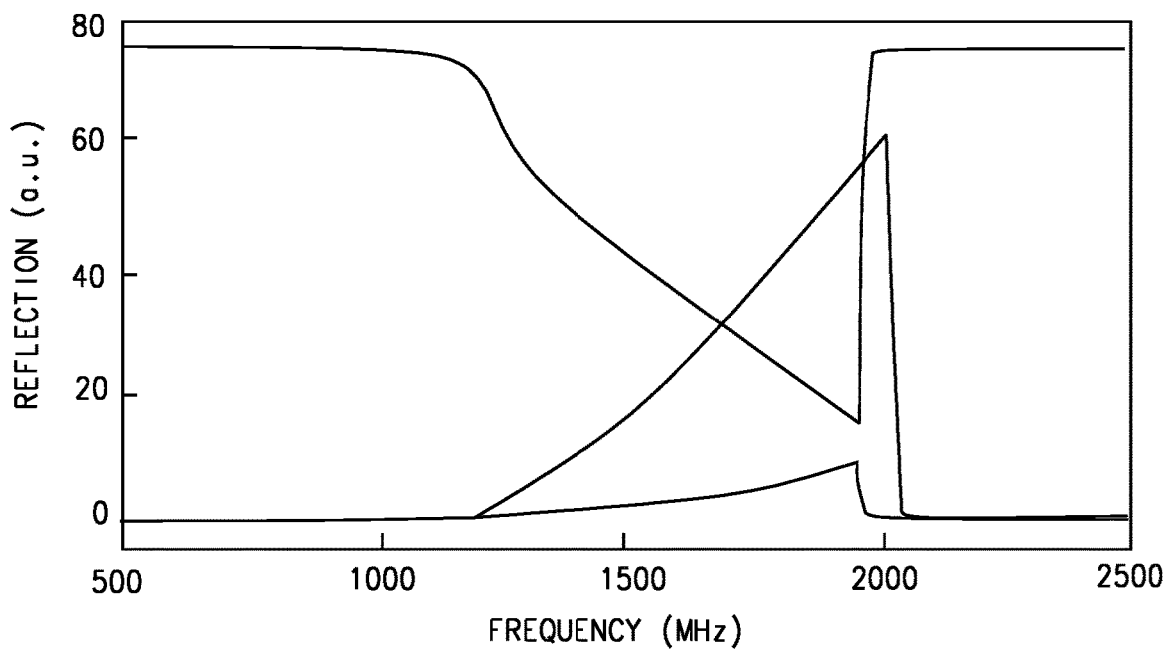

Referring to FIG. 9A, the experiment setup for back-reflection based nanoparticle detection includes a particle delivery system as described above. Referring to FIG. 9B, transmission and reflection spectra are compared at the time of 50 s and 100 s after particle deposition started. The triangular shapes of the spectra are due to opto-thermal heating of the microresonator during wavelength up-scanning.

A microresonator free of contaminations (scattering centers) should create a dark background to observe particle induced reflection, whose detection limit is constrained by the noise and sensitivity of the photo-detector. Considering two polystyrene (PS) particles with radii of R=40 nm and R=5 nm, and a resonator with Q factor of $10^8$ and mode volume of 200 mm$^3$, in the former case, mode splitting is observable and the reflected power is 250 mW with 1 mW of input power. In the latter case, no mode splitting or spectral shift is visible and but the reflected power is about 28 nW, enough for a photo-detector to measure. From these examples one can predict that in an optimized setting, this scheme has the potential to detect much smaller particles than all the demonstrated optical resonator sensing methods. For example if we consider an input power of 10 mW and a photo-detector sensitivity of 1 nW, one can detect a PS particle as small as R=1:6 nm, using a microtoroid with Q=$2\times10^8$. Using the system described in FIG. 1$a$, we first conduct the experiments with PS particles of R=50 nm. The microtoroid we used in this test has Q factors of about $5\times10^6$. The input laser power is about 5 mW. Due to the strong on-resonance pumping, the spectra exhibit triangular shapes due to the heating of resonator material and red-shift of resonance during wavelength up-scanning.

Figure 9C:
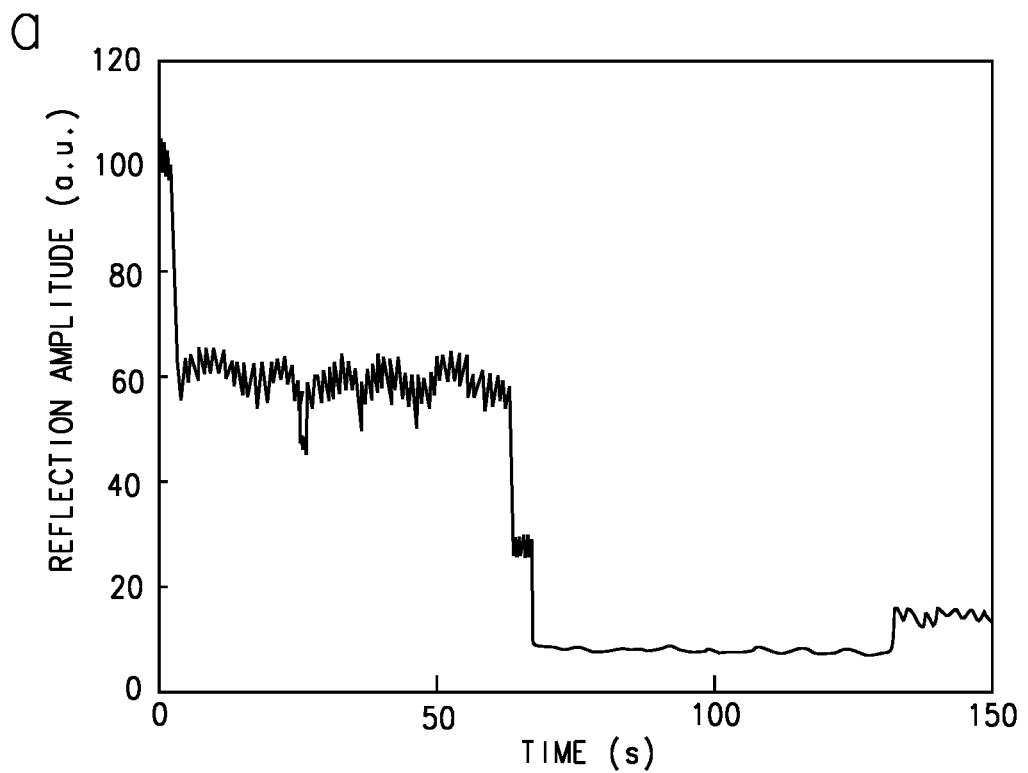
Figure 9D:
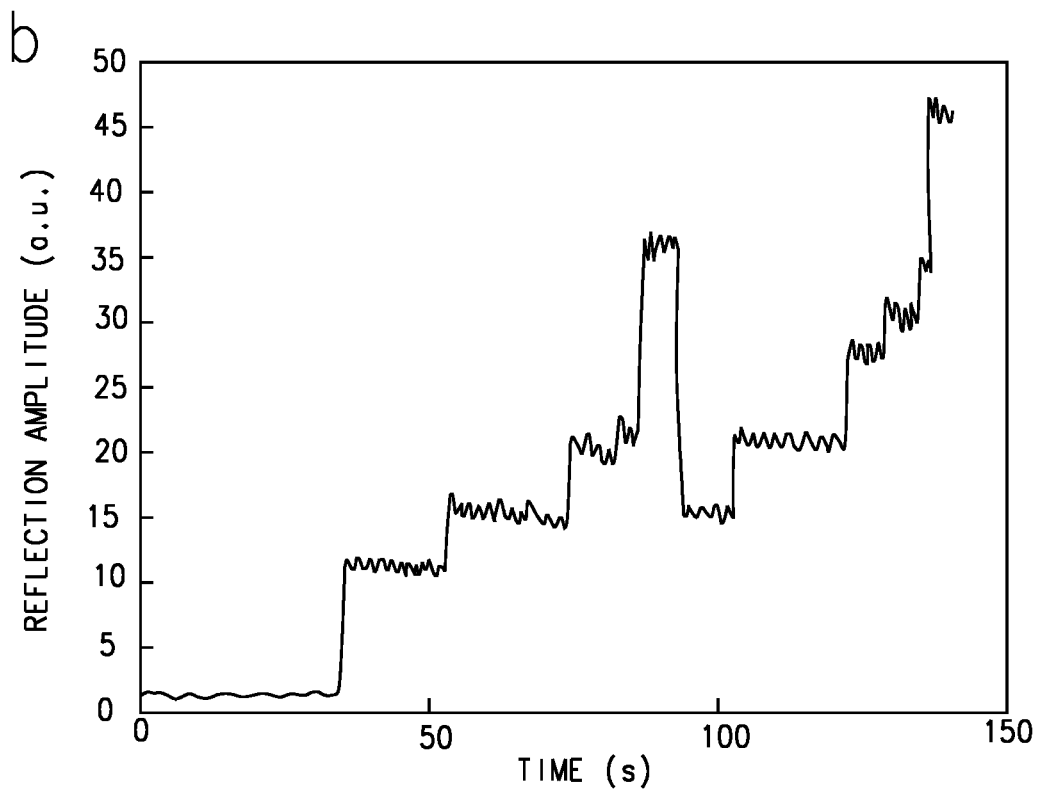

FIG. 9B depicts the captured transmission and reflection spectra at 50 and 100 seconds after particle delivery starts. Four discrete changes are seen in the first 150 s, signaling four particle binding events. Note that in this specific test, the microtoroid sample has a relatively large initial reflection before any particle binding due to contamination. The consecutively deposited particles may increase or decrease the reflection amplitude as suggested in, depending on the particle location. For a clearer presentation we plot the reflection amplitude vs. time in FIG. 9C, where the four discrete changes are shown clearly. To further test the sensitivity of the scheme, we tested with R=20 nm Sodium Chloride (NaCl) nanoparticles (n ¼ 1:52). The results are shown in FIG. 9B. The Q factor of the microtoroid in this test is about $2\times10^7$. In summary, technology as disclosed presents the theory and proof-of-principle experiments for detecting nanoparticles using the reflection mode in a microresonator. Unprecedented sensitivity could be achieved using this scheme, as indicated by both calculations and the results in the initial tests (FIGS. 9C and 9D). By further optimizing the experimental conditions, particle size range below 5 nm will be within reach.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

A micro-chip can include a processor (e.g., a central processing unit (CPU) a graphics processing unit (GPU) or both), a main memory and a static memory, which communicate with each other via a bus. A computer-readable medium or memory on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

The various implementation examples shown above illustrate a micro-resonator sensing system. A user of the present technology may choose any of the above implementations, or an equivalent thereof, depending upon the desired application. In this regard, it is recognized that various forms of the subject sensor system could be utilized without departing from the scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the sprit and scope of the present invention. Accordingly, the specification and drawings are to be regarded in an illustrative rather than a restrictive sense.

Other aspects, objects and advantages of the present invention can be obtained from a study of the drawings, the disclosure and the appended claims.

What is claimed is:

1. A wave sensing apparatus comprising:
an ultra-narrow linewidth micro-laser;
a whispering gallery mode micro-resonator;
a coupled tapered waveguide to transition the ultra-narrow linewidth micro-laser laser in and out resonance modes;
said whispering gallery mode micro-resonator having a functionalized surface of a specific material doped on the surface, wherein the specific material is responsive to the presence of a specific wave type; and
a photodetector to detect an output signal at an output port of the coupled tapered waveguide, wherein said photodetector detects a frequency shift indicative of a change in refractive index due to the functionalized surface.

2. The wave sensing apparatus as recited in claim 1, wherein the specific wave type is one or more of a magnetic wave, an IR wave, a UV wave, and an acoustic wave.

\* \* \* \* \*